US008470578B2

(12) United States Patent
Post Hansen et al.

(10) Patent No.: US 8,470,578 B2
(45) **Date of Patent: *Jun. 25, 2013**

(54) PURIFICATION OF VACCINIA VIRUSES USING HYDROPHOBIC INTERACTION CHROMATOGRAPHY

(75) Inventors: Sara Post Hansen, Hoersholm (DK); Rene Faber, Gottingen (DE); Udo Reichl, Magdeburg (DE); Michael Wolff, Biederitz (DE); Anders Peter Gram, Vaerloese (DK)

(73) Assignees: Bavarian Nordic A/S, Kvistgaard (DK); Otto-von-Guericke-Universität, Magdeburg (DE); Sartorius Stedim Biotech GmbH, Göttingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/420,892

(22) Filed: Mar. 15, 2012

(65) Prior Publication Data

US 2012/0171750 A1 Jul. 5, 2012

Related U.S. Application Data

(63) Continuation of application No. 13/214,979, filed on Aug. 22, 2011, now Pat. No. 8,163,531, which is a continuation of application No. 12/622,563, filed on Nov. 20, 2009, now Pat. No. 8,003,364, which is a continuation-in-part of application No. 12/622,474, filed on Nov. 20, 2009, now Pat. No. 8,003,363, which is a continuation-in-part of application No. 12/598,362, filed as application No. PCT/EP2008/003679 on May 7, 2008, now Pat. No. 8,012,738.

(60) Provisional application No. 60/924,413, filed on May 14, 2007.

(51) Int. Cl.

| | |
|---|---|
| ***C12N 7/00*** | (2006.01) |
| *C12N 7/01* | (2006.01) |
| *C12N 7/02* | (2006.01) |
| *C12N 15/863* | (2006.01) |
| *A61K 39/285* | (2006.01) |

(52) U.S. Cl.

USPC .................. 435/235.1; 424/199.1; 424/232.1; 435/239

(58) Field of Classification Search

None

See application file for complete search history.

(56) References Cited

U.S. PATENT DOCUMENTS

| | | | | |
|---|---|---|---|---|
| 6,641,816 | B1 * | 11/2003 | Chevalier et al. | 424/191.1 |
| 6,761,893 | B2 | 7/2004 | Chaplin et al. | |
| 8,003,363 | B2 | 8/2011 | Djurup et al. | |
| 8,003,364 | B2 | 8/2011 | Post Hansen et al. | |
| 8,012,738 | B2 | 9/2011 | Djurup et al. | |
| 2003/0138454 | A1 * | 7/2003 | Hill et al. | 424/199.1 |
| 2007/0071769 | A1 | 3/2007 | Sutter et al. | |
| 2011/0300181 | A1 | 12/2011 | Djurup et al. | |
| 2011/0306114 | A1 | 12/2011 | Post Hansen et al. | |
| 2011/0312060 | A1 | 12/2011 | Djurup et al. | |

FOREIGN PATENT DOCUMENTS

WO 2008/138533 A1 11/2008

OTHER PUBLICATIONS

Monath et al (International Journal of Infectious Diseases 852:s31-s44, 2004; in IDS).*

Abdalrhman et al. 2006. Protection induced in mice against a lethal orthopox virus by the Lister strain of vaccinia virus and modified vaccinia virus Ankara (MVA). Vaccine 24(19):4152-4160.

Amosenko et al. 1991. Use of protamine sulphate for elimination of substrate DNA in poliovaccines produced on continuous cell lines. Vaccine 9(3):207-209.

Dancis. 1978. Shear breakage of DNA, Biophys. J. 24(2):489-503.

Deshmukh et al. 2005. Adsorptive purification of pDNA on superporous rigid cross-linked cellulose matrix. Journal of Chromatography B 818(1):5-10.

Diogo et al. 2001. Studies on the retention of plasmid DNA and *Escherichia coli* nucleic acids by hydrophobic interaction chromatography. Bioseparation 10(4):211-220.

Diogo et al. 2005. Chromatography of plasmid DNA. Journal of Chromatography A 1069(1):3-22.

Diogo et al. 2000. Scale-up of hydrophobic interaction chromatography for the purification of a DNA vaccine against rabies. Biotechnology Letters 22(17):1397-1400.

Esteban et al. 1973. Early virus protein synthesis in vaccinia virus-infected cells. J Gen Virol 19(2):201-6.

Freitas et al. 2009. Plasmid purification by hydrophobic interaction chromatography using sodium citrate in the mobile phase. Separation and Purification Technology 65(1):95-104.

Gagnon et al. 2006. Simultaneous Removal of Leached Protein A, Aggregates, DNA, and Endotoxins from MAbs. BioProcess International vol. 4, No. 2: pp. 50-60 4(2):50-60.

Gijsbers et al. 2005. Quantification of Residual Host Cell DNA in Adenoviral Vectors Produced on PER.C6Â® Cells. Hum. Gene Ther. 16(3):393-398.

Goerke et al. 2005. Development of a novel adenovirus purification process utilizing selective precipitation of cellular DNA. Biotechnology and Bioengineering 91(1):12-21.

Graumann et al. 2005. Development and Scale up of Preparative HIC for the Purification of a Recombinant Therapeutic Protein. Chemical Engineering & Technology 28(11):1398-1407.

Greenberg et al. 2008. ACAM2000: a newly licensed cell culture-based live vaccinia smallpox vaccine. Expert Opinion on Investigational Drugs 17(4):555-564.

(Continued)

*Primary Examiner* — Mary E Mosher

(74) *Attorney, Agent, or Firm* — Law Office of Salvatore Arrigo and Scott Lee, LLP

(57) ABSTRACT

The present invention relates to methods for purification of Vaccinia viruses (VV) and/or Vaccinia virus (VV) particles, which can lead to highly pure and stable virus preparations of predominantly biologically active viruses. The invention encompasses purifying a virus preparation in a sterilized way with high efficiency and desirable yield in terms of purity, biological activity and stability, aspects advantageous for industrial production.

16 Claims, 3 Drawing Sheets

OTHER PUBLICATIONS

Halder et al. 2005. Adsorption of biopolymers at hydrophilic cellulose-water interface. Biopolymers 77(5):286-295.
Iuliano et al. 2002. Rapid analysis of a plasmid by hydrophobic-interaction chromatography with a non-porous resin. Journal of Chromatography A 972(1):77-86.
Joklik. 1962. The preparation and characteristics of highly purified radioactively labelled poxvirus. Biochimica et Biophysica Acta (BBA)—Specialized Section on Nucleic Acids and Related Subjects 61(2):290-301.
Jordan et al. 2009. An avian cell line designed for production of highly attenuated viruses. Vaccine 27(5):748-756.
Kalbfuss et al. 2007. Purification of cell culture-derived human influenza A virus by size-exclusion and anion-exchange chromatography. Biotechnology and Bioengineering 96(5):932-944.
Kato et al. 2004. Hydrophobic interaction chromatography at low salt concentration for the capture of monoclonal antibodies. Journal of Chromatography A 1036(1):45-50.
Knudsen et al. 2001. Membrane ion-exchange chromatography for process-scale antibody purification. Journal of Chromatography A 907(1-2):145-154.
Konz et al. 2005. Development of a Purification Process for Adenovirus: Controlling Virus Aggregation to Improve the Clearance of Host Cell DNA. Biotechnology Progress 21(2):466-472.
Kramarczyk et al. 2008. High-throughput screening of chromatographic separations: II. Hydrophobic interaction. Biotechnology and Bioengineering 100(4):707-720.
Kumar et al. 2002. Process standardization for optimal virus recovery and removal of substrate DNA and bovine serum proteins in Vero cell-derived rabies vaccine. Journal of Bioscience and Bioengineering 94(5):375-383.
Lu et al. 2009. Recent Advancement in Application of Hydrophobic Interaction Chromatography for Aggregate Removal in Industrial Purification Process Curr Pharm Biotechnol 10(4):427-433.
Madalinski et al. 1977. Purification of vaccinia virus by zonal centrifugation and analysis of viral protein composition. Acta virologica 21(2):104-108.
Mahn et al. 2005. Prediction of protein retention in hydrophobic interaction chromatography. Biotechnology Advances 23(5):359-368.
Monath et al. 2004. ACAM2000 clonal Vero cell culture vaccinia virus (New York City Board of Health strain)—a second-generation smallpox vaccine for biological defense. International Journal of Infectious Diseases 8(Supplement 2):31-44.
Opitz et al. 2009. Sulfated membrane adsorbers for economic pseudo-affinity capture of influenza virus particles. Biotechnol. and Bioeng. 103(6):1144-1154.
Opitz et al. 2007. Lectin-affinity chromatography for downstream processing of MDCK cell culture derived human influenza A viruses. Vaccine 25(5):939-947.
Opitz et al. 2008. Capture of cell culture-derived influenza virus by lectins: Strain independent, but host cell dependent. Journal of Virological Methods 154(1-2):61-68.
Påhlman et al. 1977. Hydrophobic interaction chromatography on uncharged sepharose® derivatives : Effects of neutral salts on the adsorption of proteins. Journal of Chromatography A 131:99-108.
Payne et al. 1976. Presence of Haemagglutinin in the Envelope of Extracellular Vaccinia Virus Particles. J Gen Virol 32(1):63-72.
Queiroz et al. 2001. Hydrophobic interaction chromatography of proteins. Journal of Biotechnology 87(2):143-159.
Sakata et al. 2007. Chromatographic Removal of DNA from Protein Solutions by Cationic Polymer Beads. Current Pharmaceutical Analysis 3:170-179.
Sakata et al. 2005. Chromatographic Removal of Host Cell DNA from Cellular Products Using Columns Packed with Cationic Copolymer Beads. Chromatographia 62(9):465-470.
Sheng-Fowler et al. 2009. Issues associated with residual cell-substrate DNA in viral vaccines. Biologicals 37 (3):190-195.
Stickl et al. 1970. Purifying the vaccinia virus vaccine by gel filtration. Zentralblatt fur Bakteriologie, Parasitenkunde, Infektionskrankheiten und Hygiene. 1. Abt. Medizinisch-hygienische Bakteriologie, Virusforschung und Parasitologie. 215(1):38-50.
Tauer et al. 1995. DNA clearance in chromatography of proteins, exemplified by affinity chromatography. Journal of Biochemical and Biophysical Methods 30(1):75-78.
Transfiguracion et al. 2003. Size-Exclusion Chromatography Purification of High-Titer Vesicular Stomatitis Virus G Glycoprotein-Pseudotyped Retrovectors for Cell and Gene Therapy Applications. Hum. Gene Ther. 14 (12):1139-1153.
Triyoso et al. 1999. Pulsatile shear stress leads to DNA fragmentation in human SH-SY5Y neuroblastoma cell line. The Journal of Physiology 515(2):355-365.
Tsumoto et al. 2007. Arginine improves protein elution in hydrophobic interaction chromatography: The cases of human interleukin-6 and activin-A. Journal of Chromatography A 1154(1-2):81-86.
Ueberbacher et al. 2008. Hydrophobic interaction chromatography of proteins: V. Quantitative assessment of conformational changes. Journal of Chromatography A 1198-1199:154-163.
Wolff et al. 2008. Downstream Processing: From Egg to Cell Culture-Derived Influenza Virus Particles. Chemical Engineering & Technology 31(6):846-857.
Wolff et al. 2010. Capturing of cell culture-derived modified Vaccinia Ankara virus by ion exchange and pseudo-affinity membrane adsorbers, Biotechnology and Bioengineering Processing, 105(4):761-9 (Published online Nov. 4, 2009).
World-Health-Organization. 1998. WHO Expert Commitee on Biological Standardization. Worl Health Organ. Tech. Rep. Ser. 878(i-vi):1-101.
Zwartouw et al. 1962. Purification of pox viruses by density-gradient centrifugation. Journal of General Microbiology 29:523-529.

* cited by examiner

PURIFICATION OF VACCINIA VIRUSES USING HYDROPHOBIC INTERACTION CHROMATOGRAPHY

CROSS-REFERENCE TO RELATED APPLICATIONS

This application is a continuation of U.S. application Ser. No. 13/214,979 filed Aug. 22, 2011 now U.S. Pat. No. 8,163,531, which is a continuation of U.S. application Ser. No. 12/622,563, filed Nov. 20, 2009 now U.S. Pat. No. 8,003,364, which is a continuation-in-part of U.S. application Ser. No. 12/622,474, filed Nov. 20, 2009 now U.S. Pat. No. 8,003,363, which is a continuation-in-part of U.S. application Ser. No. 12/598,362, filed Oct. 30, 2009 now U.S. Pat. No. 8,012,738, which is the U.S. National Stage of International Application No. PCT/EP2008/003679 filed May 7, 2008, which claims the benefit of U.S. Provisional Application No. 60/924,413, filed May 14, 2007, all of which are incorporated herein by reference.

BACKGROUND OF THE INVENTION

1. Field of the Invention

The invention relates to methods for purification of Vaccinia viruses (VV) and/or Vaccinia virus (VV) particles.

2. Description of Related Art

Traditionally in medicine, a vector is a living organism that does not cause disease itself, but which spreads infection by "carrying" pathogens (agents that cause disease) from one host to another. A vaccine vector is a weakened or killed version of a virus or bacterium that carries an inserted antigen (coding for a protein recognized by the body as foreign) from a disease-causing agent to the subject being vaccinated. A vaccine vector delivers the antigen in a natural way into the body and stimulates the immune system into acting against a "safe infection." The immune system is led into generating an immune response against the antigen that protects the vaccinated subject against future "risky infections."

In vaccine development, a recombinant modified virus can be used as the vehicle or vaccine vector for delivering genetic material to a cell. Once in the cell, genetic information is transcribed and translated into proteins, including the inserted antigen targeted against a specific disease. Treatment is successful if the antigen delivered by the vector into the cell produces a protein, which induces the body's immune response against the antigen and thereby protects against the disease.

A viral vector can be based on an attenuated virus, which cannot replicate in the host but is able to introduce and express a foreign gene in the infected cell. The virus or the recombinant virus is thereby able to make a protein and display it to the immune system of the host. Some key features of viral vectors are that they can elicit a strong humoral (B-cell) and cell-mediated (T-cell) immune response.

Viral vectors are commonly used by researchers to develop vaccines for the prevention and treatment of infectious diseases and cancer, and of these, poxviruses (including canary pox, vaccinia, and fowl pox) are the most common vector vaccine candidates.

Pox viruses are a preferred choice for transfer of genetic material into new hosts due to the relatively large size of the viral genome (appr. 150/200 kb) and because of their ability to replicate in the infected cell's cytoplasm instead of the nucleus, thereby minimizing the risk of integrating genetic material into the genome of the host cell. Of the pox viruses, the vaccinia and variola species are the two best known. The virions of pox viruses are large as compared to most other animal viruses (for more details see Fields et al., eds., Virology, 3rd Edition, Volume 2, Chapter 83, pages 2637 ff).

Variola virus is the cause of smallpox. In contrast to variola virus, vaccinia virus does not normally cause systemic disease in immune-competent individuals and it has therefore been used as a live vaccine to immunize against smallpox. Successful worldwide vaccination with Vaccinia virus culminated in the eradication of smallpox as a natural disease in the 1980s (The global eradication of smallpox. Final report of the global commission for the certification of smallpox eradication; History of Public Health, No. 4, Geneva: World Health Organization, 1980). Since then, vaccination has been discontinued for many years, except for people at high risk of poxvirus infections (for example, laboratory workers). However, there is an increasing fear that, for example, variola causing smallpox may be used as a bio-terror weapon. Furthermore, there is a risk that other poxviruses such as cowpox, camelpox, and monkeypox may potentially mutate, through selection mechanisms, and obtain similar phenotypes as variola. Several governments are therefore building up stockpiles of Vaccinia-based vaccines to be used either pre-exposure (before encounter with variola virus) or post-exposure (after encounter with variola virus) of a presumed or actual smallpox attack.

Vaccinia virus is highly immune-stimulating and provokes strong B- (humoral) and T-cell mediated immunity to both its own gene products and to any foreign gene product resulting from genes inserted in the Vaccinia genome. Vaccinia virus is therefore seen as an ideal vector for vaccines against smallpox and other infectious diseases and cancer in the form of recombinant vaccines. Most of the recombinant Vaccinia viruses described in the literature are based on the fully replication competent Western Reserve strain of Vaccinia virus. It is known that this strain has a high neurovirulence and is thus poorly suited for use in humans and animals (Morita et al. 1987, Vaccine 5, 65-70).

In contrast, the Modified Vaccinia virus Ankara (MVA) is known to be exceptionally safe. MVA has been generated by long-term serial passages of the Chorioallantois Vaccinia Ankara (CVA) strain of Vaccinia virus on chicken embryo fibroblast (CEF) cells (for review see Mayr, A. et al. 1975, Infection 3, 6-14; Swiss Patent No. 568,392). Examples of MVA virus strains deposited in compliance with the requirements of the Budapest Treaty are strains MVA 572, MVA 575, and MVA-BN® deposited at the European Collection of Animal Cell Cultures (ECACC), Salisbury (UK) with the deposition numbers ECACC V94012707, ECACC V00120707 and ECACC V00083008, respectively, and described in U.S. Pat. Nos. 7,094,412 and 7,189,536.

MVA is distinguished by its great attenuation profile compared to its precursor CVA. It has diminished virulence or infectiousness, while maintaining good immunogenicity. The MVA virus has been analyzed to determine alterations in the genome relative to the wild type CVA strain. Six major deletions of genomic DNA (deletion I, II, III, IV, V, and VI) totaling 31,000 base pairs have been identified (Meyer, H. et al. 1991, J. Gen. Virol. 72, 1031-1038). The resulting MVA virus became severely host-cell restricted to avian cells. The excellent properties of the MVA strain have been demonstrated in extensive clinical trials (Mayr, A. et al. 1978, Zbl. Bakt. Hyg. I, Abt. Org. B 167, 375-390; Stickl, H. et al. 1974, Dtsch. med. Wschr. 99, 2386-2392), where MVA 571 has been used as a priming vaccine at a low dose prior to the administration of conventional smallpox vaccine in a two-step program and was without any significant adverse events (SAES) in more than 120,000 primary vaccinees in Germany (Stickl, H et al. 1974, Dtsch. med. Wschr. 99, 2386-2392; Mayr et al. 1978, Zbl. Bakt. Hyg. I, Abt. Org. B 167, 375-390).

MVA-BN® is a virus used in the manufacturing of a stand-alone third generation smallpox vaccine. MVA-BN® was developed by further passages from MVA strain 571/572. To date, more than 1500 subjects including subjects with atopic dermatitis (AD) and HIV infection have been vaccinated in clinical trials with MVA-BN® based vaccines.

The renewed interest in smallpox vaccine-campaigns with Vaccinia-based vaccines has initiated an increased global demand for large-scale smallpox vaccine production. Furthermore, the use of Vaccinia virus as a tool for preparation of recombinant vaccines has additionally created significant industrial interest in methods for manufacturing (growth and purification) of native Vaccinia viruses and recombinant-modified Vaccinia viruses.

Viruses used in the manufacturing of vaccines or for diagnostic purposes can be purified in several ways depending on the type of virus. Traditionally, purification of pox viruses including Vaccinia viruses and recombinant-modified Vaccinia viruses has been carried out based on methods separating molecules by means of their size differences. To enhance removal of host cell contaminants (e.g. DNA and proteins), in particular DNA, the primary purification by means of size separation has been supplemented by secondary methods such as enzymatic digestion of DNA (e.g. Benzonase treatment). Most commonly, the primary purification of Vaccinia viruses and recombinant-modified Vaccinia viruses has been performed by sucrose cushion or sucrose gradient centrifugation at various sucrose concentrations. Recently, ultrafiltration has also been applied either alone or in combination with sucrose cushion or sucrose gradient purification.

Vaccinia Viruses-based vaccines have in general been manufactured in primary CEF (Chicken Embryo Fibroblasts) cultures. Vaccines manufactured in primary CEF cultures are generally considered safe as regards residual contaminants. First, it is scientifically unlikely that primary cell cultures from healthy chicken embryos should contain any harmful contaminants (proteins, DNA). Second, millions of people have been vaccinated with vaccines manufactured on CEF cultures without any adverse effects resulting from the contaminants (CEF proteins and CEF DNA). There is, therefore, no regulatory requirement for the level of host cell contaminants in vaccines manufactured in primary CEF cultures, but for each vaccine the manufacturer must document its safety. The regulatory concern for vaccines manufactured in primary CEF cultures relates to the risk of adventitious agents (microorganisms (including bacteria, fungi, mycoplasma/spiroplasma, mycobacteria, *rickettsia*, viruses, protozoa, parasites, TSE agent) that are inadvertently introduced into the production of a biological product).

In the current methods for purification of Vaccinia viruses, manufactured in primary CEF culture the level of CEF protein may be up to 1 mg/dose and the CEF DNA level may exceed 10 μg/dose of $1\times10^8$ as measured by the TCID50. These levels are considered acceptable from a safety and regulatory perspective as long as the individual vaccine manufacturer demonstrates that the levels to be found in the Final Drug Product (FDP) are safe at the intended human indications. Due to the risk of presence of adventitious agents in vaccines manufactured in primary cell cultures and the associated need for extensive, expensive biosafety testing of each vaccine batch manufactured, there is a strong stimulus for the vaccine industry to change to continuous cell lines. Once a continuous cell line has been characterized, the need for testing for adventitious agents of the production batches is minimal.

However, switch from primary to continuous cell culture for production of Vaccinia and Vaccinia recombinant vaccines is expected to impose stricter safety and regulatory requirements. In fact, the regulatory authorities have proposed new requirements for levels of DNA contaminants in vaccines manufactured using continuous cell lines (See Draft FDA guideline), which may be as low as 10 ng host-cell DNA/dose. To achieve such low level of host cell contaminants, new and improved methods for purification are needed.

It appears that vaccinia virions are able to bind to heparin through the surface protein A27L (Chung et al. 1998, J. Virol. 72, 1577-1585). At least three surface proteins A27L (Chung et al., J. Virol. 72(2):1577-1585, 1998; Ho et al., Journal of Molecular Biology 349(5):1060-1071, 2005; Hsiao et al., J. Virol. 72(10):8374-8379, 1998) D8L (Hsiao et al., J. Virol. 73(10):8750-8761, 1999), and H3L (Lin et al., J. Virol. 74(7): 3353-3365, 2000) of the most abundant infectious form of the Vaccinia virus have been reported to bind to glycosaminoglycans.

Examples of glycosaminoglycans in affinity chromatography applications are heparin and heparan sulfate. These are highly charged, linear and sulfated polysaccharides composed of repeating disaccharide units containing an uronic acid (glucuronic or iduronic acid) and an N-sulfated or N-acetylated glucosamine (Ampofo et al., Analytical Biochemistry 199(2):249-255, 1991; Nugent, Proceedings of the National Academy of Sciences of the United States of America 97(19):10301-10303, 2000; Rabenstein, Nat. Prod. Rep. 19:312-331, 2002).

Cellufine® sulfate and sulfated cellulose membranes are sulfated glucose polymers. Several studies reported antiviral activities of sulfated cellulose and sulfated dextran/dextrines (Baba et al., Antimicrob. Agents Chemother. 32(11):1742-1745, 1988; Chattopadhyay et al., International Journal of Biological Macromolecules 43(4):346-351, 2008; Mitsuya et al., Science 240(4852):646-649, 1988; Piret et al., J. Clin. Microbiol. 38(1):110-119, 2000), as well as the binding of virus particles to Cellufine® sulfate (O'Neil et al., Bio/Technology 11:173-178, 1993; Opitz et al., Biotechnol. and Bioeng. 103(6):1144-1154, 2009). The precise interaction between these viruses and sulfated cellulose is currently not fully understood.

It has further been suggested that affinity chromatography (Zahn, A and Allain, J.-P. 2005, J. Gen. Virol. 86, 677-685) may be used as basis for purification of certain virus preparations. There are several examples for the application of ion exchange and affinity membrane adsorbers (MA) for the purification of virus particles like adenoviral vectors (Peixoto et al., Biotechnology Progress 24(6):1290-1296, 2008; Sellick, BioPharm International 19(1):31-32, 34, 2006), *Aedes* aegyptidensonucleosis virus (Enden et al., J Theor Biol 237 (3):257-264, 2005), baculovirus (Wu et al., Hum. Gene Ther. 18(7):665-672, 2007), and influenza virus (Kalbfuss et al., Journal of Membrane Science 299(1-2):251-260, 2007; Opitz et al., Biotechnol. and Bioeng. 103(6):1144-1154, 2009; and Opitz et al., Journal of Biotechnology 131(3):309-317, 2007).

For efficient purification of vaccinia virus and recombinant vaccinia virus-based vaccines, some significant challenges need to be overcome. Vaccinia virions are far too large to be effectively loaded onto commercially available heparin columns, e.g., the Hi-Trap heparin column from Amersham Biosciences used by others (Zahn, A and Allain, J.-P. 2005, J. Gen. Virol. 86, 677-685) for lab-scale purification of Hepatitis C and B viruses. The Vaccinia virion volume is approximately 125 times larger than Hepatitis virion. (The diameter of the Vaccinia virus is, thus, appr. 250 nm as compared with the hepatitis C and B virions diameter being appr. 50 nm). Thus, available matrices as, e.g., used in the column-based approach may not allow for adequate entrance of virions into the matrix, loading of sufficient amounts of virus particles or sufficiently rapid flow through the column to meet the needs for industrial scale purification. Zahn and Allain worked with virus load up to $1\times10^6$ in up to 1.0 ml volume. For pilot-scale purification to achieve sufficient material for early clinical trials virus loading capacity higher than $1\times10^{11}$, preferably up $1\times10^{13}$, in volumes higher than 5 L, preferably up to 50 L, is needed. For industrial purification of Vaccinia virus loading capacity higher than $1\times10^{13}$, preferably higher than $1\times10^{14}$ in volumes higher than 300 L, preferably higher than 600 L, is needed.

The large size of the Vaccinia virus may prevent effective steric access between the specific surface proteins of the virions and the ligand immobilized to the matrix. Currently described lab-scale methods of use for purification of small virus particles may therefore not be industrially applicable to purification of Vaccinia virus.

Due to the high number of functional surface molecules interacting with the ligand used for binding of the Vaccinia virus particles, elution of bound Vaccinia virus may require more harsh and therefore potentially denaturing conditions to elute and recover the Vaccinia virus particles in a biologically effective form in high yields. The matrix, the ligand design, the method of ligand immobilization, and the ligand density may therefore require careful design to mediate an effective binding of the Vaccinia virus and to permit an effective elution of biologically active Vaccinia virus particles.

Vaccinia virions are too large to be sterile filtered. The method used in this invention has therefore been developed by to be applicable for an aseptic industrial-scale manufacturing process in a way ensuring full compliance with regulatory requirements regarding sterility of vaccines. In line with the above and for the purpose of this invention, the column substituted with the ligand can be applicable for sterilization-in-place or can be available as a pre-sterilized unit.

In the past, numerous methods like cesium chloride gradient centrifugation (Payne and Norrby 1976), sucrose cushion or sucrose gradient centrifugation (Esteban and Metz 1973; Joklik 1962; Madalinski et al. 1977; Zwartouw et al. 1962), tangential-flow filtration and diafiltration (Greenberg and Kennedy 2008; Monath et al. 2004), as well as size exclusion chromatography (Stickl et al. 1970), have been described for the isolation and purification of smallpox virus particles. Introduction of cell culture-derived smallpox vaccines production processes led to a reconsideration of the classic purification schemes.

Current smallpox vaccines are purified mainly after cell disruption by centrifugation and filtration methods (Abdalrhman et al. 2006; Greenberg and Kennedy 2008; Monath et al. 2004). However, residual DNA levels need to be further reduced for newly licensed vaccine products from continuous cell lines to comply with current regulations. Accordingly, biopharmaceutical product solutions used for injection should contain less than 10 ng of cellular DNA per dose (World-Health-Organization 1998) to reduce the possibilities for cellular transformations by potential oncogenic DNA (Sheng-Fowler et al. 2009) and infections by infectious DNA. Hence, DNA contaminants need to be reduced, which is commonly done for smallpox and other vaccines, as well as for viral vectors, by nuclease treatments (Greenberg and Kennedy 2008; Konz et al. 2005; Monath et al. 2004; Transfiguracion et al. 2003; Wolff and Reichl 2008).

Alternative approaches described in the literature for the clearance of host cell DNA from biopharmaceutical products are density gradient centrifugation, precipitation, anion exchange and affinity chromatography. For example Kumar et al. (Kumar et al. 2002) demonstrated the clearance of host cell DNA from rabies vaccine by density gradient centrifugation. Selective precipitation has been described for the preparation of poliovaccines (Amosenko et al. 1991) and recombinant adenoviral vectors (Goerke et al. 2005). Chromatographic approaches are frequently applied for DNA reductions in recombinant protein production processes (Gagnon et al. 2006; Knudsen et al. 2001; Sakata and Kunitake 2007; Sakata et al. 2005; Tauer et al. 1995) and viral vaccines (Kalbfuss et al. 2007; Opitz et al. 2009; Opitz et al. 2008). Recently, a downstream scheme focusing on a sequential combination of pseudo-affinity and anion exchange membrane adsorbers (MA) has been described (Wolff et al. 2009) allowing a significant reduction of DNA in cell culture-derived smallpox vaccines. However, the DNA burden needs to be still improved. Hydrophobic interaction chromatography (HIC) is routinely used in bioseparations (Graumann and Ebenbichler 2005; Kramarczyk et al. 2008; Lu et al. 2009; Mahn and Asenjo 2005; Queiroz et al. 2001; Tsumoto et al. 2007; Ueberbacher et al. 2008) since it offers an orthogonal separation technique to purification methods based on ionic interactions. HIC is influenced by many factors like ligands, ligand densities, applied salts, pH, buffer type and temperature (Graumann and Ebenbichler 2005; Kramarczyk et al. 2008; Queiroz et al. 2001).

The influence of salts on hydrophobic interactions follows the lyotropic (Hofineister) series according to their effect on the solubility of macromolecules in aqueous solutions (Graumann and Ebenbichler 2005; Kramarczyk et al. 2008; Queiroz et al. 2001). Antichaotropic salts are considered to be water structuring, whereas chaotropic ions randomize liquid water structure and those are likely to reduce the hydrophobic interaction strength (Queiroz et al. 2001). In recent years HIC gained popularity for the separation of plasmid DNA from impurities like RNA, genomic DNA, lipopolysaccharides and denatured plasmid forms (Diogo et al. 2000).

To achieve a bio-specific purification of Vaccinia virus particles with high biological activity, there is a need in the art for development of industrially usable ligands for Vaccinia virus purification. Thus, use of a ligand displaying highly specific and highly effective binding to the Vaccinia virus would be advantageous as it would improve purification by its ability to specifically sort out biologically active Vaccinia virus particles thereby increasing the purity, viability, and functionality of the purified Vaccinia virus.

BRIEF SUMMARY OF THE INVENTION

The invention encompasses methods for virus purification. The application of adsorption chromatography to capture virus particles after cell homogenization and cell debris clearance is described. The invention includes virus purification using pseudo-affinity chromatography based on heparin and sulfated cellulose and/or hydrophobic interaction chromatography based on ether, poly-propylene-glycol, phenyl, butyl, or hexyl functional groups.

A hydrophobic interaction chromatography media was used to reduce the DNA content of virus preparations. Several different hydrophobic interaction chromatography ligands were analyzed.

Pseudo-affinity membrane adsorbers, based on reinforced sulfated cellulose and heparin-membrane adsorbers, were also used. These were optimized in terms of dynamic binding capacities and contaminant depletion The combination of sulfated cellulose membrane adsorbers with a phenyl hydrophobic interaction chromatography resulted in an overall virus recovery range of 76% to 55%. DNA depletion was reduced to 0.01% of the initial starting material and the reduction of total protein achieved a protein contamination below 0.1%.

The invention encompasses methods for purifying biologically active Vaccinia viruses. In one embodiment, the method comprises loading a solid-phase matrix, to which a ligand is attached, with a biologically active Vaccinia virus contained in a liquid-phase culture, washing the matrix; and eluting the biologically active Vaccinia virus.

In one embodiment, the invention encompasses a method for the purification of biologically active Vaccinia virus comprises binding the Vaccinia virus to a solid-phase hydrophobic interaction chromatography (HIC) matrix and eluting the biologically active virus. In one embodiment, the method further comprises binding the Vaccinia virus to a solid-phase pseudo-affinity (PA) matrix; and eluting the biologically active virus.

In one embodiment, the binding the Vaccinia virus to the PA matrix is performed prior to binding the Vaccinia virus to the HIC matrix. In one embodiment, the binding the Vaccinia virus to the HIC matrix is performed prior to binding the Vaccinia virus to the PA matrix.

Preferably, the HIC matrix comprises a PPG ligand, a phenyl ligand, a butyl ligand, or a hexyl ligand.

In one embodiment, the eluted Vaccinia virus contains less than 10 ng host-cell DNA per $10^8$ virus particles. In one embodiment, the method reduces the amount of dsDNA in the eluted virus to less than 0.04% of input. In one embodiment, the method reduces the amount of dsDNA in the eluted virus to less than 0.1% of input.

In one embodiment, the PA matrix comprises or is a membrane. Preferably, the PA matrix comprises or is a sulfated cellulose matrix. More preferably, the sulfated cellulose matrix comprises or is a sulfated reinforced cellulose membrane.

In one embodiment, the PA matrix comprises or is a heparin ligand membrane.

In one embodiment, the Vaccinia virus is a recombinant Vaccinia virus. In one embodiment, the Vaccinia virus is MVA or recombinant MVA.

In one embodiment, the Vaccinia virus is eluted from the PA matrix with ammonium sulfate. In a preferred embodiment, the Vaccinia virus is eluted from the PA matrix with 1.7 M ammonium sulfate.

In one embodiment, the Vaccinia virus is eluted from the HIC matrix with a citric acid buffer.

In one embodiment, the method further comprises a purification step by ion-exchange.

In one embodiment, the purified Vaccinia virus retains at least 30% of its initial TCID50.

In one embodiment, the method further comprises administering the eluted Vaccinia virus to an animal, preferably a human.

DETAILED DESCRIPTION OF THE INVENTION

Figure 1:
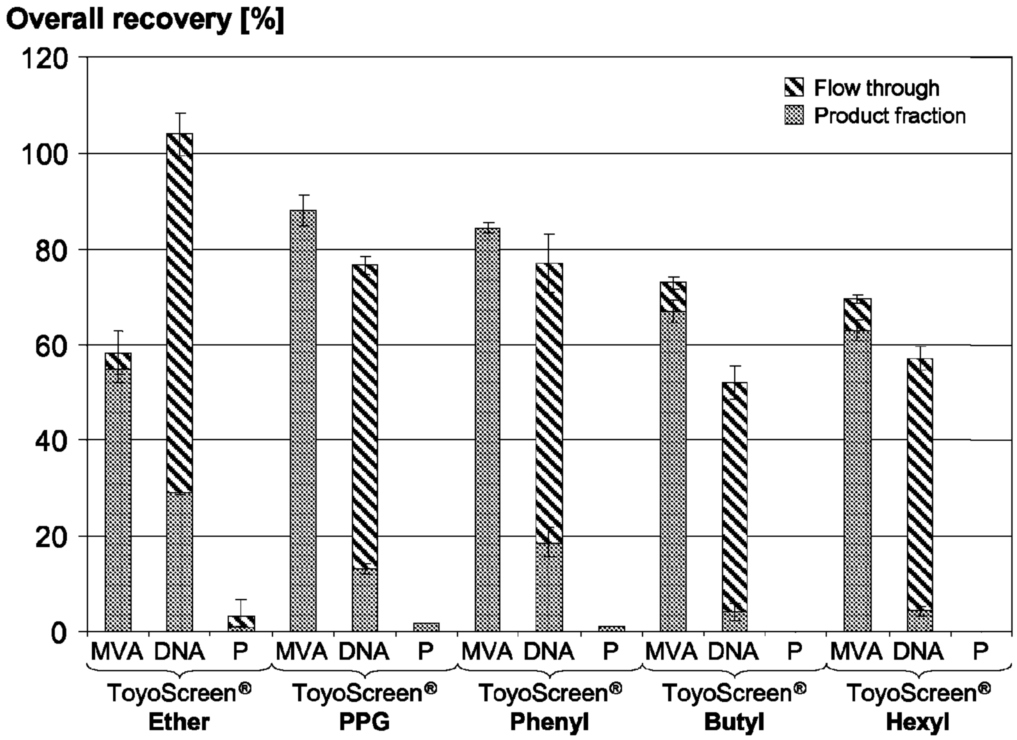
FIG. 1 depicts screening of hydrophobic interaction chromatography media. Relative amounts of virus (MVA, ELISA), total dsDNA (DNA; Quant-iT® PicoGreen® assay) and total protein (P; Pierce® BCA protein assay) during the purification of CEF cell-derived MVA-BN® virus particles using 1 ml columns of ToyoScreen® Ether, ToyoScreen® PPG, ToyoScreen® Phenyl, ToyoScreen® Butyl and ToyoScreen® Hexyl. Adsorption buffer: 1.7 M $(NH4)_2SO4$, 50 mM K2HPO4, pH 7.4; elution buffer: 50 mM K2HPO4, pH 7.4. All chromatographic experiments were conducted 3 times and the individual samples were analyzed as described in the material and method section; error bars: mean and standard deviation of each test series.

The invention encompasses methods for purifying viruses. In particular, the present invention is directed to a method for the purification of biologically active Vaccinia virus comprising:

a. loading a solid-phase matrix, to which a ligand is attached, with a Vaccinia virus contained in a liquid-phase culture;

b. washing the matrix, and c. eluting the biologically active Vaccinia virus.

The ligand is a substance that, on the one hand, can be attached to the solid-phase matrix, e.g., by binding or coupling thereto and that, on the other hand, is able to form a reversible complex with the Vaccinia virus. Thus, by interacting with the virus, the virus is reversibly retained.

The ligand can be a biological molecule as, for example, a peptide and/or a lectin and/or an antibody and/or, preferably, a carbohydrate. The ligand may also comprise or consist of sulfate. In a further embodiment, the ligand comprises one or more negatively charged sulfate groups.

Preferably, the ligand is a hydrophobic molecule as, for example, an aromatic phenyl group, a PPG group, a butyl group, or a hexyl group.

In one embodiment, the method comprises purification of Vaccinia virus with hydrophobic interaction chromatography (HIC). In a further embodiment, the method comprises purification of Vaccinia virus with HIC together with pseudo-affinity chromatography.

The use of HIC can provide high virus yields with large reductions in DNA and protein contaminants. The level of DNA contamination can be reduced to 0.01% of the initial starting material and the level of protein contamination can be reduced to below 0.1%.

Combination of sulfated cellulose based MA with HIC phenyl column chromatography allowed the purification of CEF cell culture-derived MVA-BN® virus particles at high virus yields and impressive purity levels. Protein levels were after SC-MA and HIC-phenyl chromatography purification independent of the tested production batch below 25 μg total protein per dose. Hence, protein levels would be sufficient for newly licensed cell culture-derived human vaccine products.

Current guidelines for newly licensed human vaccine products from continues cell lines dictate that residual DNA levels exceeding 10 ng per dose are not acceptable (Gijsbers et al. 2005; Sheng-Fowler et al. 2009; World-Health-Organization 1998). DNA depletion was, in some cases, sufficient to evade nuclease treatment. A further Benzonase® treatment can be included. Due to the tremendously reduced amount of DNA in the product fractions, the required amount of Benzonase® for nuclease treatment can be tremendously reduced allowing a cost-effective modification of current downstream processes. Furthermore, a small scale Benzonase® treatment reduces the probability of vaccines or viral vectors to contain intact oncogenes or further functional DNA sequences.

The invention encompasses a process based on SC-MA in combination with HIC-phenyl chromatography for a downstream process for Vaccinia virus particles in a manufacturing process and allows for economizing the required nuclease treatment step compared to classical downstream processes for small pox vaccines or MVA-BN® based viral vectors.

The ligand can be attached to the matrix directly, e.g, by direct binding, or can be attached to the matrix indirectly though another molecule, e.g. by coupling through a linker or spacer.

The solid-phase matrix can be a gel, bead, well, membrane, column, etc. In a preferred embodiment of the invention, the solid-phase comprises or is a membrane, in particular a cellulose membrane. However, a broad range of other polymers modified with specific groups capable to bind the virus can be used. Preferred are hydrophilic polymers. Examples are cellulose derivatives (cellulose esters and mixtures thereof, cellulose hydrate, cellulose acetate, cellulose nitrate); agarose and its derivatives; other polysaccachrides like chitin and chitosan; polyolefines (polypropylene); polysulfone; ployethersulfone; polystyrene; aromatic and aliphatic polyamides; polysulfonamides; halogenated polymers (polyvinylchloride, polyvinylfluoride, polyvinylidenfluoride); polyesters; homo- and copolymers of acrylnitrile.

The method and further embodiments of the invention can overcome the limitations of currently known methods preventing industrial-scale, effective purification of Vaccinia virus particles with high biological activity and purity. The method is superior in terms of yield, process time, purity, recovery of biologically active Vaccinia virus particles and costs to existing pilot-scale methods for purification of Vaccinia virus particles, which are primarily based on sucrose-cushion centrifugation and/or diafiltration or non-specific ion-exchange chromatography. It is also superior in terms of yield, process time, purity, recovery of biologically active Vaccinia virus particles, and costs to the only existing large-scale method for purification of Vaccinia virus particles, which is based on ultrafiltration, enzymatic DNA degradation, and diafiltration.

According to the present invention, Vaccinia virus can be purified under aseptic conditions to obtain a biologically active, stable, and highly pure virus preparation in high yield. The Vaccinia viruses can be native or recombinant.

The present invention provides an improved method for aseptic purification of Vaccinia viruses in lab-, pilot-, and, preferably, in industrial-scale, leading to a biologically active, stable and highly pure virus preparation in high yield.

This invention provides a more time-effective and cost-effective process for purification of Vaccinia viruses and recombinant Vaccinia viruses, Modified Vaccinia virus Ankara (MVA) and recombinant MVA, MVA-BN® and recombinant MVA-BN®, leading to a biologically active, stable and highly pure virus preparation in high yield.

In another embodiment, this invention provides virus preparations produced by the method of the invention.

Use of the eluted Vaccinia virus or recombinant Vaccinia virus, or Modified Vaccinia virus Ankara (MVA) or recombinant MVA or MVA-BN® or recombinant MVA-BN®, all preferably obtained by the method according to the present invention, for the preparation of a pharmaceutical composition, in particular a vaccine, is also an embodiment of the invention. The virus and/or pharmaceutical preparation is preferably used for the treatment and/or the prevention of cancer and/or of an infectious disease.

A method for inducing an immune response or for the vaccination of an animal, specifically of a mammal, including a human, in need thereof, characterized by the administration of a Vaccinia virus or recombinant Vaccinia virus, or Modified Vaccinia virus Ankara (MVA) or recombinant MVA or MVA-BN® or recombinant MVA-BN® vaccine prepared by a process comprising a purification step as described above is a further embodiment of the invention.

As used herein, an "attenuated virus" is a strain of a virus whose pathogenicity has been reduced compared to its precursor, for example by serial passaging and/or by plaque purification on certain cell lines, or by other means, so that it has become less virulent because it does not replicate, or exhibits very little replication, but is still capable of initiating and stimulating a strong immune response equal to that of the natural virus or stronger, without producing the specific disease.

According to a further preferred embodiment of the present invention, glucosamine glycan (GAG), in particular heparan sulfate or heparin, or a GAG-like substance is used as ligand.

As used herein, "glycosaminoglycans" (GAGs) are long un-branched polysaccharides consisting of a repeating disaccharide unit. Some GAGs are located on the cell surface where they regulate a variety of biological activities such as developmental processes, blood coagulation, tumor metastasis, and virus infection.

As used herein, "GAG-like agents" are defined as any molecule which is similar to the known GAGs, but can be modified, for example, by the addition of extra sulfate groups (e.g. over-sulfated heparin). "GAG-like ligands" can be synthetic or naturally occurring substances. Additionally, the term "GAG-like ligands" also covers substances mimicking the properties of GAGs as ligands in ligand-solid-phase complexes. One example for a "GAG-like ligand" mimicking GAG, specifically heparin, as ligand is Sulfate attached to Reinforced Cellulose as solid-phase, thus forming Sulfated Reinforced Cellulose (SRC) as ligand-solid-phase complex. The use of SRC complex is also a preferred embodiment of the present invention. Stabilized Reinforced Cellulose membranes can be obtained, for example, from Sartorius AG.

As used herein, "Bulk Drug Substance" refers to the purified virus preparation just prior to the step of formulation, fill and finish into the final vaccine.

As used herein, "Biological activity" is defined as Vaccinia virus virions that are either 1) infectious in at least one cell type, e.g. CEFs, 2) immunogenic in humans, or 3) both infectious and immunogenic. A "biologically active" Vaccinia virus is one that is either infectious in at least one cell type, e.g. CEFs, or immunogenic in humans, or both. In a preferred embodiment, the Vaccinia virus is infectious in CEFs and is immunogenic in humans.

As used herein, "contaminants" cover any unwanted substances which may originate from the host cells used for virus growth (e.g. host cell DNA or protein) or from any additives used during the manufacturing process including upstream (e.g. gentamicin) and downstream (e.g. Benzonase).

As used herein, "continuous cell culture (or immortalized cell culture)" describes cells that have been propagated in culture since the establishment of a primary culture, and they are able to grow and survive beyond the natural limit of senescence. Such surviving cells are considered as immortal. The term immortalized cells were first applied for cancer cells which were able to avoid apoptosis by expressing a telomere-lengthening enzyme. Continuous or immortalized cell lines can be created, e.g., by induction of oncogenes or by loss of tumor suppressor genes.

As used herein, "heparan sulfate" is a member of the glycosaminoglycan family of carbohydrates. Heparan sulfate is very closely related in structure to heparin, and they both consist of repeating disaccharide units which are variably sulfated. The most common disaccharide unit in heparan sulfate consists of a glucuronic linked to N-acetyl glucosamine, which typically makes up approx. 50% of the total disaccharide units.

As used herein, "heparin" is a member of the glycosaminoglycan family of carbohydrates. Heparin is very closely related in structure to heparan sulfate, and they both consist of repeating disaccharide units which are variably sulfated. In heparin, the most common disaccharide unit consists of a sulfated iduronic acid linked to a sulfated glucopyranosyl. To differentiate heparin from heparan sulfate, it has been suggested that in order to qualify a GAG as heparin, the content of N-sulfate groups should largely exceed that of N-acetyl groups and the concentration of 0-sulfate groups should exceed those of N-sulfate (Gallagher et al. 1985, Biochem. J. 230: 665-674).

As used herein, "industrial scale" or large-scale for the manufacturing of Vaccinia virus or recombinant Vaccinia virus-based vaccines comprises methods capable of providing a minimum of 50,000 doses of $1.0\times10^8$ virus particles (total minimum $5.0\times10^{12}$ virus particles) per batch (production run). Preferably, more than 100,000 doses of $1.0\times10^8$ virus particles (total minimum $1.0\times10^{13}$ virus particles) per batch (production run) are provided.

As used herein, "lab-scale" comprises virus preparation methods of providing less than 5,000 doses of $1.0\times10^8$ virus particles (total less than $5.0\times10^{11}$ virus particles) per batch (production run).

As used herein, "pilot-scale" comprises virus preparation methods of providing more than 5,000 doses of $1.0\times10^8$ virus particles (total more than $5.0\times10^{11}$ virus particles), but less than 50,000 doses of $1.0\times10^8$ virus particles (total minimum $5.0\times10^{12}$ virus particles) per batch (production run).

As used herein, "Primary cell culture", refers to the stage where the cells have been isolated from the relevant tissue (e.g. from specific pathogen free (SPF) hens eggs), but before the first sub-culture. This means that the cells have not been grown or divided any further from the original origin.

As used herein, "Purity" of the Vaccinia virus preparation or vaccine is investigated in relation to the content of the impurities DNA, protein, Benzonase, and gentamicin. The purity is expressed as specific impurity, which is the amount of each impurity per dose (e.g. ng DNA/dose).

As used herein, "purification" of a Vaccinia virus preparation refers to the removal or measurable reduction in the level of some contaminant in a Vaccinia virus preparation.

As used herein, "Recombinant Vaccinia virus" is a virus, where a piece of foreign genetic material (from e.g. HIV virus) has been inserted into the viral genome. Thereby, both the Vaccinia virus genes and any inserted genes will be expressed during infection of the Vaccinia virus in the host cell.

As used herein, "Stability" means a measure of how the quality of the virus preparation (Bulk Drug Substance (BDS) or Final Drug Product (FDP)) varies with time under the influence of a variety of environmental factors such as temperature, humidity and lights, and establishes a retest period for the BDS or a shelf-life for the FDP at recommended storage conditions (Guidance for industry Q1A (R2).

As used herein, a "Virus preparation" is a suspension containing virus. The suspension could be from any of the following steps in a manufacturing process: after virus growth, after virus harvest, after virus purification (typically the BDS), after formulation, or the final vaccine (FDP).

As used herein "vaccinia virus forms" refer to the three different types of virions produced by infected target cells: Mature virions (MV), wrapped virions (WV), and extra-cellular virions (EV) (Moss, B. 2006, Virology, 344:48-54). The EV form comprises the two forms previously known as cell-associated enveloped virus (CEV), and extra-cellular enveloped virus (EEV) (Smith, G. L. 2002, J. Gen. Virol. 83: 2915-2931).

The MV and EV forms are morphologically different since the EV form contains an additional lipoprotein envelope. Furthermore, these two forms contain different surface proteins, which are involved in the infection of the target cells by interaction with surface molecules on the target cell, such as glycosaminoglycans (GAGs) (Carter, G. C. et al. 2005, J. Gen. Virol. 86: 12791290). The invention involves use of the purification of all forms of Vaccinia Virus.

The different forms of Vaccinia virions contain different surface proteins, which are involved in the infection of the target cells by interaction with surface molecules on the target cell, such as glycosaminoglycans (GAGs) (Carter, G. C. et al. 2005, J. Gen. Virol. 86: 1279-1290). These surface proteins will as mentioned supra be referred to as receptors. On the MV form, a surface protein named p14 or A27L (the latter term will be used in this application) is involved in the initial attachment of the virions to the target cell. A27L binds to GAG structures on the target cell prior to entry into the cell (Chung C. et al. 1998, J. Virol. 72: 1577-1585), (Hsiao J. C. et al. 1998 J. Virol. 72: 8374-8379), (Vazquez M. et al. 1999, J. Virol. 73: 9098-9109) (Carter G. C. et al. 2005, J. Gen. Virol. 86: 1279-1290). The natural ligand for A27L is presumed to be the GAG known as heparan sulfate (HS). Heparan Sulfate belongs to a group of molecules known as glycosaminoglycans (GAGs). GAGs are found ubiquitously on cell surfaces. (Taylor and Drickamer 2006, Introduction to Glycobiology, $2^{nd}$ edition, Oxford University Press). GAGs are negatively charged molecules containing sulfate groups. The A27L protein is located on the surface of the virions and is anchored to the membrane by interaction with the A17L protein (Rodriguez D. et al. 1993, J. Virol. 67: 3435-3440) (Vazquez M. et al. 1998, J. Virol. 72: 10126-10137). Therefore, the interaction between A27L and Al17L can be kept intact during isolation in order to retain full biological activity of the virions. The specific nature of the protein-protein interaction between A17L and A27L has not been fully elucidated, but it has been suggested that a presumed "Leucine-zipper" region in the A27L is involved in the interaction with A17L (Vazquez M. et al. 19981, J. Virol. 72: 10126-10137).

The invention encompasses the use of the affinity interaction between the A27L surface protein on the MV form and glucosaminoglycans, in particular Heparan Sulfate, for purification of the MV form of Vaccinia Virus.

The term "ligand", thus, refers both to a receptor on a target cell and to the specific binding structure attached to a solid-phase matrix used for purification of Vaccinia.

The same principle as described above can be applied to interactions between other target cell surface structures and other Vaccinia surface proteins of the MV form participating in the Vaccinia virus' recognition of, attachment to, entry into and/or fusion with the target cell. The entire A27L protein, or fragments thereof containing the binding region for the GAG ligand can be used as agents to elute Vaccinia viruses-GAG complexes from a solid-phase column of the invention. Fragments can be readily generated by routine molecular techniques and screened for their ability to dissociate Vaccinia viruses-GAG complexes using routine techniques known in the art, such as by measuring eluted, biologically active virus.

The presumed native GAG-ligand for the MV form of Vaccinia is Heparan Sulfate (HS) and can be one of the suitable ligands. The invention also comprises use of "non-native" ligands for purification of Vaccinia virus. Such non-native ligands are compounds with a high degree of structural and/or conformational similarity to native ligands. As an example, Heparin, which is a close analogue to the native ligand for A27L, HS, can be used for affinity-purification of MV form by interaction with the A27L surface protein, see further below. Heparin has been shown to partially inhibit the binding between target cells and Vaccinia virus and can therefore also be used for affinity purification of the MV form of Vaccinia. Other GAG-ligands and GAG-like ligands can also be used.

In one embodiment of the invention, Heparan Sulfate, used for affinity purification of the MV form of Vaccinia, binds A27L on biologically active Vaccinia viruses, but does not bind inactive Vaccinia viruses or Vaccinia virus fragments.

The purification of Vaccinia virus using HIC allows for a large decrease in the level of cellular DNA contamination of the viral preparation. Thus, a ether, poly-propylene glycol (PPG), phenyl, butyl or hexyl ligand can be employed.

The ligand makes possible the elution of the bound Vaccinia virus under such mild conditions that the Vaccinia virus fully retain their biologically activity. This means that virus is infectious, for example in CEF cells. The infectivity of the Vaccinia virus can be preserved during purification such that at least 10%, 20%, 30%, 40%, 50%, 60%, 70%, 80%, or 90% of the initial $TCID_{50}$ is retained during purification. Preferably, at least 30% of the initial $TCID_{50}$ is retained during purification. The purification can further comprise a step of binding to a pseudo-affinity (PA) matrix. As used herein, a "pseudo-affinity (PA) matrix" is a solid-phase matrix with an attached pseudo-affinity (PA) ligand. As used herein, a "pseudo-affinity (PA) ligand" is a GAG or GAG-like ligand that binds to Vaccinia virus virions.

The binding and elution characteristics for the GAG-ligand substituted matrix depend not only on the individual characteristics of the matrix and ligand, but also on the interplay between the two.

By modifying, e.g., the ligand density or by attaching, e.g. binding or coupling of, the ligand to the matrix by "arms" or "spacers" of different length and chemical characteristics (hydrophobicity, hydrophilicity) the binding strength between the target ligand structure and Vaccinia virus can be altered, which can be used to enhance the capture or ease the elution.

To enhance the purification method, the matrix in the form of a chromatography gel or membrane to be used for the purification preferably:

Has a high pore size (to make as many ligands as possible accessible to the Vaccinia virus)

Has a rigid structure to allow for fast flow rates

Is available in a form permitting direct or indirect attachment, e.g. by binding or coupling, of ligands Is applicable for sterilization in place or available as a pre-sterilized unit, e.g. by using radiation.

In one embodiment, the solid phase matrix is a gel or membrane with a pore size of 0.25 μm, preferably of more than 0.25 μm, more preferably of 1.0-3.0 μm demonstrating a linear flow rate under actual purification conditions of 10 cm/min, preferably 20 cm/min. The pore size of the matrix can be 0.25-0.5 μm, 0.5-0.75 μm, 0.75-1.0 μm, 1.0-2.0 μm, 2.0-3.0 μm, or greater than 3.0 μm.

In one embodiment, with the solid phase matrix containing a heparan sulfate as an immobilized ligand, the virus harvest from the upstream virus growth process is loaded in a crude (unpurified) form with a flow rate of 10 cm/min, preferably 20 cm/min at a virus concentration of $10^6$ virions per mL in pilot scale and $10^7$ virions per mL in industrial scale.

In one embodiment, there are three steps in the purification process of the invention, which are common for most affinity chromatography processes:

1) Loading of Vaccinia virus or Vaccinia recombinant virus onto the solid phase;

2) Washing of the solid phase to remove contaminants; and

3) Elution of the Vaccinia virus or recombinant virus to be isolated.

Step 1. Loading of Vaccinia Virus or Recombinant Virus onto a Solid-Phase Matrix Loading the solid phase with a ligand can be performed by a batch-, column- or membrane approach.

The membrane approach can have some benefits, specifically for large bio-molecules, in particular for large viruses like Vaccinia viruses: For example, large pore sizes and the availability of the ligand on the surface of the membrane allow high binding capacities of even large viral particles. The membrane approach is, thus, a preferred embodiment of the present invention.

In all embodiments mentioned above, the Vaccinia virus or recombinant virus to be isolated is present in a liquid phase. When the Vaccinia virus or recombinant virus gets close to the ligand, the Vaccinia virus will bind specifically to or be "captured by" the ligand, thereby the Vaccinia virus or recombinant Vaccinia virus can be temporarily immobilized on the solid phase, while the contaminants will remain in the liquid phase.

By appropriate selection of the ligand type, ligand density and ligand steric configuration, the binding parameters of Vaccinia virus to the solid phase can be altered, thereby providing means for optimization of the purification parameters.

In one embodiment, the virus is bound to the ligand in ammonium sulphate, for example, at 0.3M, 0.45M, 0.6M, 0.85M, 1.0M, 1.25M, 1.5M, 1.7M, 1.85M, or 2.0M.

In various embodiments, the virus is bound to the ligand in citric acid, for example at 100 mM, or with $K_2HPO_4$, for example at 50 mM at pH7.4. In preferred embodiments, the virus is bound in ammonium sulphate containing 50 mM $K_2HPO_4$ at pH7.4.

Step 2. Washing of the Solid Phase to Remove Contaminants

When the binding of the biologically active Vaccinia viruses or recombinant viruses to the ligand has proceeded sufficiently, the host cell contaminants (in particular host cell DNA and proteins) that remain in the liquid phase can be removed by washing the solid phase, to which the Vaccinia virus is bound, with an appropriate washing medium.

In one embodiment, the solid phase is washed with ammonium sulphate, for example, at 0.3M, 0.45M, 0.6M, 0.85M, 1.0M, 1.25M, 1.5M, 1.7M, 1.85M, or 2.0M.

In various embodiments, the solid phase is washed with citric acid, for example at 100 mM, or with $K_2HPO_4$, for example at 50 mM at pH7.4.

Step 3. Eluting the Vaccinia Virus or Recombinant Virus by Specific or Non-Specific Agents The biologically active Vaccinia viruses or recombinant viruses can be eluted. The elution of the captured Vaccinia virus can be performed, for example, by:

Agents specifically disrupting the specific interaction between the ligand and a L surface protein on the Vaccinia virus (to be called specific agents), or by Agents non-specifically disrupting the electrostatic interaction between the ligand and the surface protein (to be called non-specific agents).

In one embodiment, the agent is ammonium sulphate, for example, at 0.3M, 0.45M, 0.6M, 0.85M, 1.0M, 1.25M, 1.5M, 1.7M, 1.85M, or 2.0M.

In various embodiments, the agent is citric acid, for example at 100 mM, or $K_2HPO_4$, for example at 50 mM at pH7.4.

According to further embodiments of the present invention, the Vaccinia virus is eluted with GAG or a GAG-like ligand or part thereof, with the GAG-binding domain of A27L or part thereof, and/or with an 0-glycoside-binding cleaving enzyme.

In another embodiment, the agent is sodium chloride, more preferably, an increasing NaCl concentration gradient ranging from 0.15 M to 2.0 M.

Pre-Treatment

Prior to loading on the solid phase, a pre-treatment of the virus suspension can be performed, specifically in order to remove contaminants from the Vaccinia virus in the liquid-phase culture.

Pre-treatment can be one or more of the following steps either alone or in combination:

1) Homogenization of the host cells

Ultrasound treatment

Freeze/thaw

Hypo-osmotic lysis

High-pressure treatment

2) Removal of cell debris

Centrifugation

Filtration

3) Removal/reduction of host cell DNA

Benzonase treatment

Cationic exchange

Selective precipitation by cationic detergents

According to a further embodiment of the invention, the pH value of the viral suspension is decreased just prior to loading in order to improve the binding of the virus particle to the ligand. The pH value of the viral suspension can be decreased from appr. pH 7.0-8.0 to 4.0-6.9, in particular to pH 4.0, 4.2, 4.4, 4.5, 4.6, 4.8, 5.0, 5.2, 5.4, 5.5, 5.6, 5.8, 6.0, 6.2, 6.4, 6.5, 6.6, 6.8, 6.9. Preferably, the pH value is decreased from pH 7.0-8.0 to pH 5.8. Subsequently, just after loading and before elution, the pH value is again increased to pH 7.0-8.0, in particular to pH 7.0, 7.2, 7.4, 7.5, 7.6, 7.8, 8.0, preferably to pH 7.7, in order to improve the stability of the viral particles.

Post-Treatment

Depending on the agent used for elution of the Vaccinia virus or recombinant virus, post-treatment can be performed to enhance the purity of the virus preparation. The post-treatment could be ultra/diafiltration for further removal of impurities and/or specific or non-specific agents used for elution. To obtain an efficient purification of the virus, it is also preferred to combine the purification according to the invention with one or more further purification steps, e.g., by ion-exchange(s). Ion-exchange(s) can, then, also be performed as post-treatment step(s).

In order to prevent aggregation of the purified virus suspension and, thus, to, inter alia, improve the detection of infectious particles, in particular by the $TCID_{50}$ method, it can also be suitable to increase the pH value after elution of the virus, in particular to a pH value of up to 9 or more, in particular to pH 7.5, 7.6, 7.8, 8.0, 8.2, 8.4, 8.5, 8.6, 8.8, 9.0, 9.2, 9.4, 9.5, 9.6, 9.8, 10.0, 10.2, 10.4, 10.5. Preferably, the pH value is increased from, in particular, pH 7.0, 7.2, 7.4, 7.5, 7.6, 7.8, 8.0, preferably pH 7.7 to pH 9.0.

Preferably, the amount of host-cell DNA in a VV dose of $1\times10^8$ $TCID_{50}$ is 10-20 μg, 1-10 μg, 100 ng-1 μg, 10-100 ng, or 1-10 ng. In various embodiments, the amount of host-cell DNA is less than 100 ng, 50 ng, 20 ng, 10 ng, 5 ng, or 1 ng per ml or less than 100 ng, 50 ng, 20 ng, 10 ng, 5 ng, or 1 ng. The amount of dsDNA in a VV sample can be reduced by the purification method to less than 40%, 20%, 10%, 5%, 2.5, 1%, 0.5%, 0.25%, 0.1%, 0.05%, 0.02% or 0.01% of input.

In various embodiments, the amount of protein in the purified VV is less than 250 μg/ml, 100 μg/ml, 50 μg/ml, 20 μg/ml, 10 μg/ml, or 5 μg/ml. In various embodiments, the amount of protein in the purified VV is less than 250 μg/$1\times10^8$ $TCID_{50}$, 100 μg/$1\times10^8$ $TCID_{50}$, 50 μg/$1\times10^8$ $TCID_{50}$, 20 μg/$1\times10^8$ $TCID_{50}$, 10 μg/$1\times10^8$ $TCID_{50}$, or 5 μg/$1\times10^8$ $TCID_{50}$. The amount of contaminating protein is preferably less than 40%, 20%, 10%, 5%, 2.5, 1%, 0.5%, 0.25%, 0.1%, 0.05%, 0.02% or 0.01% of input.

The practice of the invention employs techniques in molecular biology, protein analysis, and microbiology, which are within the skilled practitioner of the art. Such techniques are explained fully in, for example, Ausubel et al. 1995, eds, Current Protocols in Molecular Biology, John Wiley & Sons, New York.

Modifications and variations of this invention will be apparent to those skilled in the art. The specific embodiments described herein are offered by the way of example only, and the invention is not to be construed as limited thereby. Additional aspects and advantages of the invention will be set forth in part in the description which follows, and in part will be obvious from the description, or may be learned by practice of the invention.

In one embodiment, the invention provides a more time-effective and cost-effective process for purification of Vaccinia viruses and recombinant-modified Vaccinia viruses in higher yield, comprising one or more of the following steps:

a. loading a solid-phase matrix with a liquid-phase virus preparation, wherein the solid-phase matrix comprises a ligand appropriate for interacting with the virus, e.g. by reversibly binding the virus b. washing of the matrix, and c. eluting the virus.

In a preferred embodiment, the method comprises the following steps:

a. Loading a column, membrane, filter or similar solid-phase matrix comprising one or more appropriate virus-binding ligands with a liquid-phase virus preparation, b. Washing of the matrix with an appropriate solvent to remove contaminants, and c. Eluting the Vaccinia virus with an appropriate solvent to achieve a highly pure, biologically active, stable virus preparation.

In a further preferred embodiment, the method comprises the following steps:

a. Loading a column, membrane, filter or similar solid-phase matrix comprising one or more appropriate HIC ligands with a liquid-phase virus preparation b. Washing of the matrix with an appropriate solvent to remove contaminants, and c. Eluting the Vaccinia virus with citric acid, for example at 100 mM, or $K_2HPO_4$, for example at 50 mM at pH7.4, to achieve a highly pure, biologically active, stable virus preparation.

In one particularly preferred embodiment, the method is used for the purification of biologically active Vaccinia virus and comprises the following steps:

a. Loading a column, membrane, filter or similar solid-phase HIC matrix substituted with a phenyl or PPG group with a Vaccinia virus preparation dissolved in a neutral buffer (pH 6.5 to 8.5, preferably >=pH 7.5) in ammonium sulphate, preferably at 1.5-1.7M, b. Washing of the matrix with a sufficient amount of the loading buffer to ensure complete elution of all non-binding Vaccinia virus particles and non-binding contaminants, and c. Eluting the Vaccinia virus with citric acid, for example at 100 mM, or $K_2HPO_4$, for example at 50 mM at pH7.4 to obtain the biologically active Vaccinia virus particles.

In another particularly preferred embodiment, the method is used for the purification of biologically active Vaccinia virus and comprises the following steps:

a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M, or citric acid, at 100 mM, or $K_2HPO_4$ at 50 mM at pH7.4.

b. Washing of the matrix with a sufficient amount of the loading buffer to ensure complete elution of all non-binding Vaccinia virus particles and non-binding contaminants, for example, as measured by the return of the 280 nm absorbance signal to the pre-loading baseline, and c. Eluting the Vaccinia virus with 1.5-1.7M ammonium sulphate containing 50 mM $K_2HPO_4$ at pH7.4.

In another particularly preferred embodiment, the method is used for the purification of biologically active Vaccinia virus and comprises the following steps:

a. Loading a column, membrane, filter or similar solid-phase sulphated cellulose matrix with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M, or citric acid, at 100 mM, or $K_2HPO_4$ at 50 mM at pH7.4.

b. Washing of the matrix with a sufficient amount of the loading buffer to ensure complete elution of all non-binding Vaccinia virus particles and non-binding contaminants, for example, as measured by the return of the 280 nm absorbance signal to the pre-loading baseline, and c. Eluting the Vaccinia virus with 1.5-1.7M ammonium sulphate containing 50 mM $K_2HPO_4$ at pH7.4.

In another particularly preferred embodiment, the method is used for the purification of biologically active Vaccinia virus and comprises the following steps:

a. Loading a column, membrane, filter or similar solid-phase matrix substituted with a Heparin (HP) with a Vaccinia virus preparation dissolved in a neutral buffer (pH 6.5 to 8.5, preferably >=pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M, or citric acid, at 100 mM, or $K_2HPO_4$ at 50 mM at pH7.4.

b. Washing of the matrix with a sufficient amount of the loading buffer to ensure complete elution of all non-binding Vaccinia virus particles and non-binding contaminants, for example, as measured by the return of the 280 nm absorbance signal to the pre-loading baseline, c. Eluting the Vaccinia virus with 1.5-1.7M ammonium sulphate containing 50 mM $K_2HPO_4$ at pH7.4, d. Loading a column, membrane, filter or similar solid-phase HIC matrix with the eluted Vaccinia virus preparation, e. Washing of the matrix with a sufficient amount of the loading buffer to ensure complete elution of all non-binding Vaccinia virus particles and non-binding contaminants, and f. Eluting the Vaccinia virus with citric acid, for example at 100 mM, or $K_2HPO_4$, for example at 50 mM at pH7.4 to obtain the biologically active Vaccinia virus particles.

In another particularly preferred embodiment, the method is used for the purification of biologically active Vaccinia virus and comprises the following steps:

a. Loading a column, membrane, filter or similar solid-phase sulphated cellulose matrix with a Vaccinia virus preparation dissolved in a neutral buffer (pH 6.5 to 8.5, preferably >= pH 7.5) with a physiological salt concentration (approximately 150 mM NaCl). An appropriate buffer is Phosphate Buffered Saline (PBS), e.g. 0.01 to 0.1 M phosphate, 0.15 M NaCl, pH 7.5. Other appropriate buffers are Tris-NaCl, e.g. 0.01 to 0.1 M Tris, 0.15 M, or citric acid, at 100 mM, or $K_2HPO_4$ at 50 mM at pH7.4.

b. Washing of the matrix with a sufficient amount of the loading buffer to ensure complete elution of all non-binding Vaccinia virus particles and non-binding contaminants, for example, as measured by the return of the 280 nm absorbance signal to the pre-loading baseline, and c. Eluting the Vaccinia virus with 1.5-1.7M ammonium sulphate containing 50 mM $K_2HPO_4$ at pH7.4, d. Loading a column, membrane, filter or similar solid-phase HIC matrix with the eluted Vaccinia virus preparation, e. Washing of the matrix with a sufficient amount of the loading buffer to ensure complete elution of all non-binding Vaccinia virus particles and non-binding contaminants, and f. Eluting the Vaccinia virus with citric acid, for example at 100 mM, or $K_2HPO_4$, for example at 50 mM at pH7.4 to obtain the biologically active Vaccinia virus particles.

EXAMPLE 1

Production of Modified Vaccinia Ankara Virus Particles

MVA-BN® virus particles were produced by Bavarian Nordic NS (Denmark) in primary cultures of CEF cells under Good Manufacturing Practice conditions (Vollmar et al., 2006). Different batches of the starting material were provided after homogenization and clarification as a liquid frozen product, stored in aliquots at −80° C. The initial $TCID_{50}$ values of the samples were calculated.

EXAMPLE 2

Total Protein Assay

Total protein concentrations were determined in triplicates by the Pierce® BCA protein assay reagent kit (Cat.#23225, Pierce Biotechnology, USA) as recently described (Wolff et al. 2009). The assay was calibrated against albumin standards (BSA) (Cat.#23209, Thermo Fisher Scientific Inc., USA) within the validated working range of 25 to 250 μg/ml (limit of detection: 8.3 μg/ml; limit of quantification: 25 μg/ml).

EXAMPLE 3

Quantification of MVA-BN® Virus Particles

Total MVA-BN® virus particles were quantified in triplicates by a sandwich ELISA as described previously (Wolff et al. 2009).

Infectious MVA-BN® virus particles were determined by the 50% tissue culture infective dose assay ($TCID_{50}$) in Vero cells (ECACC; Cat.#88020401, UK; $2.0\times10^5$ cells/well) as a variation of the procedure described by Jordan et al. (Jordan et al. 2009). Briefly, Vero cells were maintained in high glucose (4.5 g/l) DMEM-medium (Cat.# E15-009, PAA Laboratories GmbH, Cölbe, Germany) containing 4 mM glutamin (Cat.# G-3126-250G Sigma-Aldrich, München, Germany), 0.1% gentamycin (Cat.#15710080, Invitrogen, Karlsruhe, Germany) and 10% FBS (Cat.#3302-P280703, PAN-Biotech GmbH, Aidenbach, Germany) at 37° C. and 5% $CO_2$. Serial 10-fold dilutions of the virus containing samples were added to Vero monolayers. After incubation (48 h) the cells were fixed with a 1:2 acetone (Cat.# CP40.3, Carl Roth, Karlsuhe, Germany): methanol (Cat.#106018, Merck, Darmstadt, Germany) mixture and incubated with a polyclonal rabbit anit-vaccinia virus antibody (Cat.#220100717, Quartett Immunodiagnostika & Biotechnologie GmbH, Berlin, Germany) at 1:1000 dilution in PBS containing 1% FBS. Subsequently, the wells were washed with PBS and incubated with the secondary antibody (anit-rabbit IgG, peroxidase conjugated, Cat.# W401 B, Promega GmbH, Mannheim, Germany) in PBS containing 1% FBS. The peroxidase enzyme of the secondary antibody catalyses a color reaction upon incubation with ACE substrate solution (0.3 mg/ml 3-amino-9-ethylcarbazole (Cat.# A5754-10G, Sigma-Aldrich, München, Germany) in 0.1 M Na-acetate buffer pH 5.0 containing 0.015% $H_2O_2$ (Cat.#1.07209.0250, Merck, Darmstadt, Germany). Infected forci were identified under the light microscope and the $TCID_{50}$ is calculated from the maximum dilution of MVA-BN® suspension that yields positive dye reaction. All titrations were performed in parallel replicates.

EXAMPLE 4

DNA-Quantification Assays

The dsDNA measurements in a validated working range from 4 to 1000 ng/ml were done as described by Opitz et al. (Opitz et al. 2007) using the Quant-iT™ PicoGreen® dsDNA reagent from Molecular Probes, Inc. (Cat.# P7581, Eugene, Oreg., USA). Calibration was done against lambda DNA (Cat.# D1501, Promega Corporation, Madison, Wis., USA) within the validated working range of 4 to 1000 ng/ml (weighted regression; limit of detection: 0.66 ng/ml; limit of quantification: 2.36 ng/ml) using 100 mM citric acid buffer pH 7.2 for dilutions.

Total DNA measurements in a range of 6 to 400 pg/ml were done by the total DNA Threshold assay method after protease treatment and DNA extraction.

EXAMPLE 5

Protease Treatment

Samples were dialysed (5000 kDa MWCO; Cat.#131192, Sectrum Europe B.V., Breda, Netherlands) against 50 mM phosphate buffered saline containing 1 mM EDTA and 0.05% $NaN_3$, pH 7.0 and appropriately diluted in the Zero Calibrator solution (50 mM PBS, 1 mM EDTA, 0.05% $NaN_3$, pH 7.0; Cat.# R 8004, MDS Analytical Technologies, Ismaningen, Germany) containing 0.01 mg/ml SDS (Cat.# L 6026, Sigma-Aldrich, München, Germany) and 0.01 mg/ml Proteinase K (Cat.# P8102S, New England Biolabs GmbH, Frankfurt, Germany) and incubated over night at 56° C.

EXAMPLE 6

DNA Extraction

The DNA was extracted after protease treatment using a DNA extractor kit (Cat.#295-58501, Wako Chemicals GmbH, Neuss, Germany) according to the manufactures instructions.

EXAMPLE 7

DNA Quantification

DNA Quantification was done by the Threshold Total DNA Assay Kit (Cat.# R 9009, MDS Analytical Technologies, Ismaning, Germany) and workstation (MDS Analytical Technologies, Ismaning, Germany) as described in the following. After extraction, samples were adjusted to 500 μl with zero calibrator solution and heat denatured at 105° C. for 15 min. 1000 μl of a mixture containing biotin-conjugated, high affinity, single-stranded DNA binding protein, streptavidine and urease-conjugated monoclonal antibody against single-stranded DNA (ssDNA) were added to each sample or standard and incubated for 1 hour at 37° C. The reaction mixtures were transferred to individual wells in the manifold of the Threshold workstation. Mixtures were filtered through the biotin-coated nitrocellulose membrane adsorber under controlled vacuum. Subsequently, the wells were washed (wash solution, phosphate buffered saline, pH 6.5 containing 0.05% $NaN_3$ and 0.05% Tween 20) and the filtration was continued under high vacuum until all wells were dry. Then the dipstick membrane adsorbers were transferred to the Threshold reader which contained the substrate urea (600 μl of 5 M urea containing 0.05% $NaN_3$ and 30 μl wash solution) and the lightaddressable potentiometric sensor. Captured urease in the DNA-protein complexes hydrolyses urea which results in detectable pH changes in the substrate solution. All samples were measured in triplicates. The assay was calibrated against calf thymus DNA and all samples were analyzed additionally by spiking them with (50 pg) calf thymus DNA in order to estimate spike recoveries according to the manufacturer's recommendations. All the controls were within the range indicated on the certificate of analysis from the supplier.

EXAMPLE 8

Chromatography Materials

Pseudo-Affinity Membrane Adsorbers

Heparin-MA was a research product of Sartorius Stedim Biotech GmbH, Göttingen, Germany. It was based on reinforced stabilized cellulose with a pore size >3 μm and adsorption area of 3×75 $cm^2$ by 3×15 layers. The housing material was polypropylene. Sulfated cellulose MA (SC-MA) with a diameter of 25 mm (pore size >3 μm, Sartorius Stedim Biotech GmbH, Göttingen, Germany) were prepared as described previously (Opitz et al. 2009), except that the membrane discs were incubated for 12 hours at 35° C., 40° C. and 45° C. The adsorption area was 75 $cm^2$, and 15 membrane discs were stacked in a stainless steel membrane holder (Cat.#1980-002, GE Healthcare, München, Germany). Membrane adsorbers prepared at 40° C. have been applied for the majority of experiments, other membranes were used to optimize the sulfation degree in terms of dynamic binding capacity and purity. Sulfate ion content of blank and modified sulfated cellulose MA was estimated by the Schöniger decomposition method followed by ion exchange chromatography (Currenta GmbH & Co. OHG, Leverkusen, Germany)

Hydrophobic Interaction Chromatography Matrices

Experiments were done with 1 ml columns of the ToyoScreen HIC Mix Pack (Cat.#21398, Tosoh Bioscience GmbH, Stuttgart, Germany). The screened resins comprised ToyoScreen® Hexyl-650C, ToyoScreen® Butyl-600M, ToyoScreen® Phenyl-650M, ToyoScreen® PPG-600M, ToyoScreen® Ether 650M.

EXAMPLE 9

Adsorption Chromatography

Chromatography was performed using an Äkta Explorer system (GE Healthcare, München, Germany) at a flow rate of 1.0 ml/min and monitored by UV (280 nm) and light scattering (90°, Dawn EOS, Wyatt Technology Europe GmbH, Dernbach, Deutschland) detection.

Dynamic binding capacity of the HIC-chromatography media was determined loading the clarified MVA-BN® virus sample (1.85×$10^8$ $TCID_{50}$/ml) in adsorption buffer (1.7 M $(NH_4)_2SO_4$+50 mM $K_2HPO_4$, pH 7.4; HIC (1.7)) onto equilibrated (HIC (1.7) adsorption buffer) 1 ml columns of the HIC-columns. The breakthrough was monitored via light scattering detector and the virus particles were eluted with 50 mM $K_2HPO_4$, pH 7.4.

Dynamic binding capacities of the pseudo-affinity MA (SC-MA and heparin-MA) were determined loading the clarified MVA-BN® virus sample (1.85×$10^8$ and 4.65×$10^7$ $TCID_{50}$/ml) in SC-MA adsorption buffer (100 mM citric acid, pH 7.4) at a flow rate of 1 ml/min onto equilibrated (SC-MA adsorption buffer) 75 $cm^2$ SC-MA and heparin-MA. The breakthrough was monitored via light scattering detector and the virus particles were eluted with 100 mM citric acid containing 2 M NaCl, pH 7.4. The eluted product fraction was dialysed against adsorption buffer with a MWCO of 5000 kDa (Cat.#131192, Spectrum Europe B.V., Breda, Netherlands) and the virus and DNA content was quantified as described above.

Characterization of the HIC-materials was done with 4 ml of the clarified MVA-BN® virus sample (4.65×$10^7$ $TCID_{50}$/ml) in HIC (1.7) and HIC (1.5; 1.5 M $(NH_4)_2SO_4$+50 mM $K_2HPO_4$, pH 7.4) adsorption buffer. Prior to sample loading the chromatography material was equilibrated with the respective HIC adsorption buffers. After a brief washing (respective HIC adsorption buffer) the bound virus particles were eluted with elution buffer (50 mM $K_2HPO_4$, pH 7.4). Resulting fractions were pooled and analyzed for virus and contaminant compositions. Chromatographic materials were regenerated after each run with 10 column volumes of 0.5 M NaOH and 0.1 M HCl. All experiments were performed in triplicates.

Optimization of the Ammonium Sulfate Concentration for the MVA-BN® Adsorption onto HIC-Phenyl Resin The study was done as the characterization of the different HIC-matrices described above. However, the HIC-adsorption buffer for the sample loading and column equilibration varied. The tested adsorption buffers contained 0.45, 0.6, 0.85, 1.0, 1.25, 1.5 and 1.7 M $(NH_4)_2SO_4$ and 50 mM $K_2HPO_4$, pH 7.4.

Combination of Pseudo-Affinity MA and HIC

The chromatography was performed using the same system and monitored as described above at a flow rate of 1.0 ml/min. Four ml of the clarified MVA-BN® virus sample (4.65×$10^7$ $TCID_{50}$/ml) in 100 mM citric acid, pH 7.4 or 50 mM $K_2HPO_4$, pH 7.4 have been subjected to an equilibrated (100 mM citric acid, pH 7.4 or 50 mM $K_2HPO_4$, pH 7.4) SC-MA (75 $cm^2$) or heparin-MA (225 $cm^2$). The virus was eluted from the pseudo-affinity MA after a brief washing (100 mM citric acid, pH 7.4 or 50 mM $K_2HPO_4$, pH 7.4) in HIC (1.5 and 1.7) adsorption buffer. The pooled eluted fractions were directly loaded onto an equilibrated (respective HIC-adsorption buffer) ToyoScreen® Phenyl-650M or ToyoScreen® PPG-600M column. The adsorbed virus particles were desorbed after washing (respective HIC-adsorption buffer) from the HIC-matrices with 50 mM $K_2HPO_4$ pH 7.4 or 100 mM citric acid pH 7.4. Pooled fractions were stored at −80° C. The virus content and the amount of total dsDNA and protein were determined from representative samples as described above. Analytical samples removed were considered in the overall mass balances.

Optimization of the Pseudo-Affinity Membrane Adsorbers

Table 1 demonstrates the dependence of the cellulose sulfation on the chemical reaction temperature. Reaction temperatures of 35, 40 and 45° C. resulted in 5.5, 9.3 and 13 weight % sulfation of the cellulose backbone. The dynamic binding capacity up to 50 ml (9.3×$10^9$ $TCID_{50}$) MVA-BN® was not affected by the degree of sulfation. However, the performance in terms of product adsorption and DNA depletion varied among the tested SC-MA. The SC-MA modified at the lowest reaction temperature reflects the modest amount of adsorbed virus particles (66%). In contrast, SC-MA sulfated at 40° C. and 45° C. yielded a product recovery of 79% and 80%, respectively. The amount of total DNA in the product fraction increased with the degree of sulfation. The relative amount of DNA based on the starting material in the product was for the SC-MA produced at 35° C., 40° C. and 45° C. 7.4%, 14% and 17%, respectively. The unmodified cellulose backbone bound 15% DNA whereas 31% of the MVA-BN® virus particles adsorbed to it. Recent studies demonstrated the encouraging performance of pseudo-affinity MA based on sulfated cellulose compared to ion exchange MA (Wolff et al. 2009). These studies were conducted with MA sulfated at a reaction temperature of 37° C. and suffered from losses (36%; (Wolff et al. 2009)) of virus particles during the adsorption process.

Table 1 indicates that elevated cellulose sulfation lead within the tested temperature range to improved adsorption of the MVA-BN® virus particles. The level of sulfation also seems to affect the DNA adsorption. Higher sulfated SC-MA resulted in enhanced adsorption of total DNA (Tab. 1). In contrast un-sulfated (<0.05 wt %) cellulose disks adsorbed 15% of the initial DNA content compared to 7.4% of the least sulfated (5.5 wt %) SC-MA. This phenomenon can be explained by different interaction modes between sulfated and un-sulfated cellulose and DNA-molecules. The adsorption of DNA to hydrophilic surfaces like cellulose is commonly known and described in the literature as e.g. the partial adsorption of nucleic acids to cellulose powder (Halder et al. 2005) and the adsorption of non-circular DNA to a highly porous cellulose matrix (Deshmukh and Lali 2005). Enlarged DNA adsorption at an increasing degree of sulfation is unexpected due to the ionic phosphate groups of nucleic acids. However, previous studies with CEF cell-derived MVA-BN® virus particles displayed compared to anion exchange MA a limited adsorption of dsDNA to weak cation exchange MA and to the cationic pseudo-affinity MA like sulfated cellulose and heparin as well as the bead-based sulfated cellulose resin Cellufine® sulfate (Wolff et al. 2009). Opitz et al. demonstrated similarly the adsorption of host cell DNA during the primary capturing step of MDCK cell-derived influenza virus particles to strong and weak cation exchange MA (Opitz et al. 2009).

Table 1: Effect of the sulfation degree from sulfated cellulose on the dynamic binding capacity, purity and overall virus yield. Relative amounts (mean and standard deviation of triplicates) for MVA-BN® (ELISA) and dsDNA (Quant-iT® PicoGreen® assay) content were calculated based on the starting material of the homogenized and clarified virus broth. The adsorption area of the SC-MA was 75 $cm_2$. Equilibration and wash buffer was 100 mM citric acid, pH 7.4, and the elution buffer 100 mM citric acid+2 M NaCl, pH 7.4. The product recoveries from the cellulose backbone (blank) and the sulfated cellulose MA were estimated from 2 chromatographic experiments. The dynamic binding capacity experiments were done twice.

TABLE 1

| | | Dynamic Binding Capacity | | Recoveries in Product Fraction | |
|---|---|---|---|---|---|
| Chromatography Media | Sulfation [wt %] | Volume [ml] | Total $TCID_{50}$ [$TCID_{50}$] | MVA-BN ® [%] | Total DNA [%] |
| Cellulose backbone | <0.05 | n.d. | n.d. | 31 ± 0.2 | 15 ± 0.4 |
| SC-MA 35° C. | 5.5 | >50 | >9.3 x $10^9$ | 66 ± 3.3 | 7.4 ± 1.5 |
| SC-MA 40° C. | 9.3 | >50 | >9.3 x $10^9$ | 79 ± 2.4 | 14 ± 0.6 |
| SC-MA 45° C. | 13 | >50 | >9.3 x $10^9$ | 80 ± 6.7 | 17 ± 0.5 |

Dynamic Binding Capacities of the Tested HIC-Resins and Pseudo-Affinity MA

Table 2 shows the dynamic binding capacities of the tested chromatography materials. The capacity of all tested HIC resins was greater than 20 ml of the homogenized and clarified harvest (3.7×$10^9$ $TCID_{50}$). After 20 ml the addition of MVA-BN® virus sample was stopped, because the dynamic binding capacity was judged sufficient for the characterization of the HIC columns. The capacity of the heparin-MA was 6.0 ml corresponding to 1.1×$10^9$ $TCID_{50}$, and the capacity of the SC-MA as already discussed was independent of the degree of sulfation greater than 50 ml (9.3×$10^9$ $TCID_{50}$; Tab. 1). The high dynamic binding capacity for the SC-MA was verified via quantification of the viral particles after elution from the SC-MA and compared with data obtained during the characterization of the SC-MA. The recovered virus particles based on the loaded sample for 50 ml and 4 ml were 81% and 79%, respectively. The un-adsorbed virus particles were for the respective experiments 22% and 23%. Thus, it can be assumed that the virus particles of 9.3×$10^9$ $TCID_{50}$ did adsorb to the MA and filtration effects at a pore size of 3 to 5 μm, if at all, are negligible. Furthermore, these experiments confirm that non-specific binding to the chromatography materials at the selected volume for the characterization studies (4 ml) were insignificant. Loading of the MVA-BN® virus sample during the dynamic binding capacity studies was stopped after 50 ml to conserve sample. Earlier studies demonstrated the high dynamic binding capacity for Cellufine® sulfate, a commercial bead based resin constituted of sulfated cellulose beads, supporting the observed high capacity of SC-MA (Wolff et al. 2009).

Table 2: Dynamic binding capacity of the tested chromatography materials. The adsorption buffer for the hydrophobic interaction chromatography media (1 ml column) was 1.7 M $(NH_4)_2SO_4$+50 mM $K_2HPO_4$, pH 7.4 and for the pseudo-affinity membrane adsorbers (gray; adsorption area: 75 $cm^2$) 100 mM citric acid, pH 7.4.

TABLE 2

| | | | Breakthrough | |
|---|---|---|---|---|
| Chromatography Media | Functional Groups | N | Volume (ml) | Total $TCID_{50}$ ($TCID_{50}$) |
| ToyoScreen ® Ether | Ether | 2 | >20 | >3.7 x $10^9$ |

TABLE 2-continued

| Chromatography Media | Functional Groups | N | Breakthrough Volume (ml) | Breakthrough Total $TCID_{50}$ ($TCID_{50}$) |
|---|---|---|---|---|
| ToyoScreen ® PPG | Poly-propylene-glycol | 3 | >20 | >3.7 × $10^9$ |
| ToyoScreen ® Phenyl | Phenyl | 3 | >20 | >3.7 × $10^9$ |
| ToyoScreen ® Butyl | Butyl | 2 | >20 | >3.7 × $10^9$ |
| ToyoScreen ® Hexyl | Hexyl | 2 | >20 | >3.7 × $10^9$ |
| Heparin-MA | Heparin | 3 | 6.0 | 2.8 × $10^8$ |
| SC-MA (40° C.) | Sulfated cellulose | 3 | >50 | >2.3 × $10^9$ |

Screening of HIC Resins

Preliminary studies with NaCl (2 M), an intermediate chaotropic salt did not lead to sufficient adsorption of virus particles or nucleic acids (data not shown) to ethyl, phenyl and hexyl ligands. Hence, the suitability of HIC for the depletion of contaminating DNA after pseudo-affinity chromatography was evaluated during this study with a strong antichaotropic salt, ammonium sulfate, with a series of different hydrophobic ligands. Selection of the most promising HIC-ligands was conducted in experiments comprising the following ligands: ether, poly-propylene glycol (PPG), phenyl, butyl, and hexyl. The outcomes of these experiments are combined in FIG. 1. The majority of MVA-BN® virus particles adsorbed to the tested HIC-resins. For the PPG and phenyl ligand, no virus particles were detected via ELISA in the flow through fraction under the applied conditions. In case of the ether, butyl and hexyl HIC-ligands 3%, 6% and 7%, respectively, of the initial amount of virus were detected in the flow through fraction. However, the overall material balances for the MVA-BN® virus particles could not be closed and relative amounts of virus detected in the product fraction ranged from 55% (ether) to 88% (PPG). For phenyl, butyl and hexyl ligands 84%, 67% and 63%, respectively, of the initial amount of virus were measured in the product fraction.

The fraction of un-adsorbed DNA varied for the tested HIC-resins with ether (75%), PPG (64%), phenyl (58%), butyl (48%) and hexyl (53%; FIG. 1). The amount of co-eluted DNA with virus particles was for the different HIC-ligands as ether (29%), PPG (13%), phenyl (19%) and for butyl and hexyl 4%. Here, an increase in hydrophobicity with growing n-alkyl chain length (Queiroz et al. 2001) lead to an elevated portion of strong bound DNA, resulting in a reduced overall recovery of DNA. For the more hydrophobic ligands like butyl and hexyl 48% and 43% of the initial DNA content could not be accounted for in the material balances. Strong bound DNA were presumably removed from the HIC-resins during the regeneration step. The hydrophobic character as confirmed in these experiments is frequently exploited for the purification of plasmid DNA (Diogo et al. 2001; Diogo et al. 2005; Freitas et al. 2009; luliano et al. 2002). These applications benefit from the relatively high hydrophobicity of genomic DNA due to the exposure of the hydrophobic bases, compared to plasmid DNA molecules, where the majority of the bases are shielded inside the double helix (Freitas et al. 2009). The presented results clearly reveals that the hydrophobic character of free DNA from the MVA-BN® cultivation broth can be utilized to remove residual DNA from MVA-BN® virus particles after pseudo-affinity chromatography.

Proteins were heavily adsorbed to all tested HIC-resins under the tested conditions. Except for the ether ligand, were 2% of the initial protein content did not adsorb to the resin, no proteins were determined in the flow through for all other HIC-materials. The applied elution conditions in absence of ammonium sulfate, was not sufficient to desorb the proteins from the HIC-resins. The amount of total protein in the product fraction ranged from the detection limit (butyl, hexyl) to 2% (PPG). The product fractions of the ether and phenyl HIC-ligands contained 1% total protein. The majority of remaining proteins on the matrix were removed from the HIC-adsorbers during the harsh regeneration procedure. Any effects on dynamic capacity losses have not been observed within the tested range during the studies. However, if HIC adsorbers are applied as an orthogonal purification step to the pseudo-affinity membrane adsorbers, the majority of proteins are already removed and the overall capacity of the HIC-resins will not be significantly affected by the remaining protein load.

The high MVA-BN® recovery and DNA depletion of the PPG and phenyl HIC resins lead to the selection of these resins to explore their performance for a MVA-BN® vaccine downstream process in combination with an upstream pseudo-affinity chromatography.

Studies Combining Pseudo-Affinity MA and HIC

Table 3 illustrates the amount of MVA-BN® virus particles and DNA in the product fraction relative to the loaded sample. These experiments were conducted with 2 different batches of MVA-BN® virus (batch A and B) under different buffer conditions. Here, virus particles were adsorbed and eluted from the chromatography materials via potassium phosphate or citric acid buffers containing ammonium sulfate according to the respective studies. The applied chromatography media were sulfated cellulose- and heparin-MA (pseudo-affinity MA) and the HIC-phenyl and HIC-PPG resins. Studies conducted with batch A involved any possible combination of the two different pseudo-affinity and HIC adsorption media (Table 3).

Table 3: Purification of two different batches (A and B) of MVA-BN® virus particles by a sequential combination of pseudo-affinity membrane adsorbers (sulfated cellulose (SC-MA) and heparin (heparin-MA; gray highlighted)) and 1 ml hydrophobic interaction chromatography columns (Phenyl and PPG). Relative amounts (mean and standard deviation of triplicates) for MVA-BN® (ELISA), dsDNA content (Quant-iT® PicoGreen® assay) were calculated based on the starting material of the homogenized and clarified virus broth. Total DNA amounts labeled by a star were determined by the Threshold system in place of the Quant-iT® PicoGreen® assay. The adsorption areas of the SC-MA and heparin-MA were 75 cm2 and 225 $cm^2$, respectively. Pseudo-affinity equilibration and wash buffer was 100 mM citric acid, pH 7.4 or 50 mM potassium phosphate buffer, pH 7.4 as stated in the table, the pseudo-affinity elution buffer corresponded the HIC-adsorption buffer (1.7 M $(NH_4)_2SO_4$, pH 7.4) and the HIC elution buffers were 50 mM $K_2HPO_4$, pH7.4 or 100 mM citric acid, pH 7.4. Individual chromatographic runs were done in triplicates from which the means and standard deviations were calculated.

TABLE 3

| | Recoveries in Product Fraction | | | | | |
|---|---|---|---|---|---|---|
| | Batch A | | | | Batch B | |
| Chromatography | MVA-BN ® [%] | | Total DNA [%] | | MVA-BN ® [%] | Total DNA [%] |
| Medium | $K_2HPO_4$ | Citric acid | $K_2HPO_4$ | Citric acid | Citric acid | Citric acid |
| SC-MA | 73 ± 1.7 | 75 ± 1.6 | 5.8 ± 3.9 | 4.9 ± 0.6 | 81 ± 3.1 | 10 ± 0.4 |
| HIC-Phenyl | 76 ± 0.5 | 74 ± 5.1 | 0.9 ± 0.4[b] | 0.2 ± 0.0[b] | 94 ± 1.1 | 5.6 ± 1.4 |
| Overall recovery | 55 | 56 | 0.04 | 0.01 | 76 | 0.6 |
| Heparin-MA | 68 ± 4.2 | 68 ± 0.6 | 12 ± 4.1 | 20 ± 0.7 | 62 ± 1.7 | 19 ± 2.8 |
| HIC-Phenyl | 73 ± 1.1 | 76 ± 1.9 | 0.3 ± 0.2[b] | 0.3 ± 0.0[b] | 71 ± 4.1 | 13 ± 1.9 |
| Overall recovery | 50 | 50 | 0.04 | 0.06 | 44 | 2.5 |
| SC-MA | 77 ± 5.6 | 71 ± 2.7 | 2.0 ± 0.6 | 4.9 ± 0.6 | n.d. | n.d. |
| HIC-PPG | 64 ± 1.8 | 62 ± 1.7 | LOQ[a] | LOQ[a] | n.d. | n.d. |
| Overall recovery | 49 | 44 | LOQ[a] | LOQ[a] | n.d. | n.d. |
| Heparin-MA | 71 ± 2.4 | 59 ± 2.8 | 14 ± 0.5 | 20 ± 0.5 | n.d. | n.d. |
| HIC-PPG | 47 ± 1.4 | 60 ± 2.6 | LOQ[a] | LOQ[a] | n.d. | n.d. |
| Overall recovery | 33 | 35 | LOQ[a] | LOQ[a] | n.d. | n.d. |

[a] limit of quantification, total protein concentration of all samples has been below the quantification limit; [b] determined via DNA Threshold assay Final desorptions of the MVA-BN® product were done for all studies with potassium phosphate and citric acid buffers as described above.

Potential batch to batch variations were briefly explored by the application of a second batch (batch B) of MVA-BN® virus particles. Combinations with the HIC-PPG columns were not carried out on grounds of the low virus recoveries for the studies with batch A. Furthermore, final desorptions were done only with citric acid buffer as no differences between the potassium phosphate and citric acid buffer was observed in the initial studies and citric acid may be beneficial to reduce potential virus aggregations due to the high negative charge at neutral pH. The bulk of MVA-BN® virus in the product fraction after SC-MA chromatography ranged for experiments with potassium phosphate and citric acid from 73% to 77% and 75% to 71%, respectively. The amount of total DNA varied for the potassium phosphate and citric acid experiments from 5.8% to 2.0% and 4.9% to 4.2%, respectively. Hence, no significant differences between the individual set of experiments were encountered. However, virus yields were improved compared to previous reports (65%; (Wolff et al. 2009) as already discussed. DNA depletions were comparable to the previously reported values (Wolff et al. 2009).

Observations from the chromatographic performance of sulfated cellulose chromatography media like SC-MA or bead based sulfated cellulose (Cellufine® sulfate) for cell culture-derived influenza virus particles (Opitz et al. 2009) and MVA-BN® (Wolff et al. 2009) supporting the described results. The quantity of MVA-BN® virus in the product fraction after heparin-MA chromatography ranged for the experiments with potassium phosphate and citric acid from 68% to 71% and 59% to 68%, respectively. The amount of total DNA varied for the potassium phosphate experiments from 12% to 14% and for both sets of the citric acid experiments 20% were co-eluted with the product.

Virus recoveries after loading the homogenized and clarified harvest onto the HIC-PPG and HIC-phenyl columns differed significantly from the recoveries after subjecting the pseudo-affinity chromatography processed samples over the same HIC columns. The MVA-BN® virus recoveries for the homogenized harvest were 88% and 84% for the HIC-PPG and HIC-phenyl column, respectively. On the contrary, average virus recoveries for the pseudo-affinity chromatography purified samples achieved over all four HIC-PPG and HIC-phenyl experimental series were 58% and 75%, respectively. The increased losses are expected due to the differences in sample load and here in particular due to the heavily reduced protein load after pseudo-affinity chromatography, which could influence the adsorption behavior of the remaining virus particles.

As expected from the results of the individual unit operations, the buffer systems did not impact heavily the overall virus recoveries. Focusing on the citric acid buffered experiments optimal virus yields were accomplished with the SC-MA/HIC-phenyl combination (56%) followed by the heparin-MA/HIC-phenyl (50%), SC-MA/HIC-PPG (44%) and the heparin-MA/HIC-PPG (35%; Tab. 3). Due to the low overall virus recoveries for the HIC-PPG combinations residual DNA levels were only tested via the PicoGreen® assay and not further characterized via the Threshold assay system. Final DNA amounts in the product fractions varied for the SC-MA/HIC-phenyl combination insignificantly between 0.04% and 0.01% of the starting material (Threshold assay, Tab. 3).

However, initial tests exploring batch to batch variations by repeating some of the experiments with batch B of homogenized and clarified harvest resulted in an increased residual DNA content in the product fraction in particular after the HIC-phenyl chromatography. The DNA content in the final product fraction was for the SC-MA/HIC-phenyl and the heparin-MA/HIC-phenyl combination using virus batch B 0.6% and 2.5% (Tab. 3), respectively. While the DNA content after the pseudo-affinity chromatography using the heparin-MA was comparable, for the SC-MA there was a two-fold increase. Main differences arised from the HIC-phenyl step, resulting in a 30 to 40-fold increase of the final DNA content in batch B compared to batch A (Tab. 3).

Absolute amounts of total DNA were higher in the virus harvest for batch A than for batch B. Hence, it is not likely that capacity limitations of the HIC-adsorber could have lead to increasing residual DNA in the product fraction from batch B. Structural changes on the DNA-molecules may lead to these batch to batch variations. The integrity of DNA molecules during the production process is mainly susceptible to cellular nucleases and shear, leading to fragmentation or structural changes. The activity and amount of free cellular nucleases depends on the host cell viability during the final stages of the cultivation, which frequently varies. Shear stress should not vary heavily during the production process in the bioreactor. However, during the harvesting and clearance filtration this could potentially vary and shear induced DNA fragmentation is commonly known and has been described in several publications (Dancis 1978; Triyoso and Good 1999).

Overall virus yields varied between the two tested chromatographic combinations. For the SC-MA/HIC-phenyl combination using citric acid containing buffers the virus yield was 56% (batch A) and 76% (batch B) and for the heparin-MA/HIC-phenyl arrangement 50% (batch A) and 44% (batch B). For the heparin-MA/HIC-phenyl downstream process the product yields from both unit operations (batch B) were slightly reduced leading to an overall reduction of 6% compared to batch A. On the other hand, both unit operations of the SC-MA/HIC-phenyl set up resulted in significant increased virus recoveries, leading to approximately 20% increased yield. The small variations between the different buffer systems and upstream applied pseudo-affinity MA for batch A (50% to 56%) compared to the virus recovery of 76% and 44% for batch B leads to the conclusion that the performance of both unit operations depict a noteworthy batch to batch variation which needs to be further explored for a routine application of the downstream process for MVA-BN® vaccine products. However, batch to batch variations of biotechnological products are common and need to be further addressed in process stability evaluations.

Figure 2:
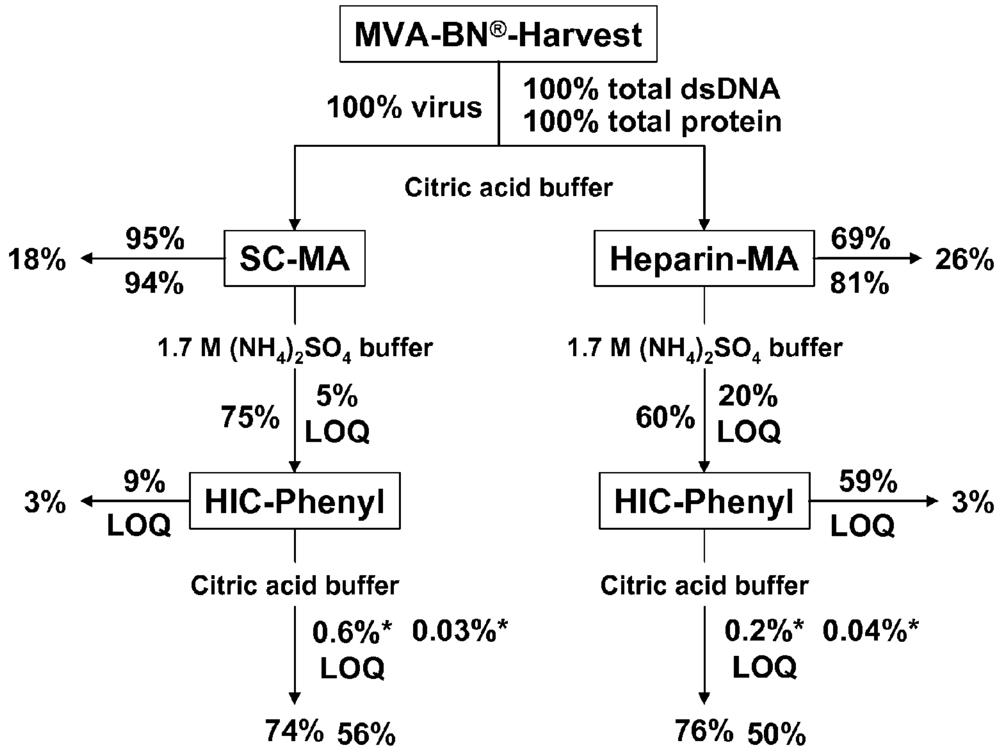
FIG. 2 depicts purification of MVA-BN® (batch A) by a combination of a SC-MA (15 layers, d=25 mm, A=75 $cm^2$) or heparin-MA (3×15 layers, d=25 mm, A=225 $cm^2$) with a 1 ml HIC-phenyl column (ToyoScreen® Phenyl-650M). The loading and equilibration buffer for the SC-MA and heparin-MA was 100 mM citric acid, pH 7.4 and the elution buffer 1.7 M $(NH_4)_2SO4$, 50 mM $K_2HPO_4$, pH 7.4. The loading and equilibration buffer for the HIC-phenyl column corresponded to the elution buffer of the pseudo-affinity MA. The elution buffer of the HIC-phenyl column was 100 mM citric acid, pH 7.4. The flow rate for the entire process was 1 ml/min. The relative virus content was monitored by an ELISA; relative amounts of total protein and dsDNA were quantified by the Pierce® BCA protein assay and the Quant iT™ PicoGreen® assay, respectively, based on the initially loaded amounts. All chromatographic experiments were done in triplicates. The ELISA and total protein analysis of individual samples were conducted in triplicates and the dsDNA measurements in duplicates.

Protein concentrations were after both tested combinations of pseudo-affinity and HIC-phenyl chromatography purifications below the quantification range of 25 μg/ml total protein (FIG. 2). After 10 fold concentrations (lyophilization and buffer adaptation) of representative HIC chromatography product fractions the limit for the quantification range was still not reached. The final protein concentration after the characterized combined purification steps was below 25 μg per dose.

Optimization of Ammonium Sulfate Concentration

Figure 3:
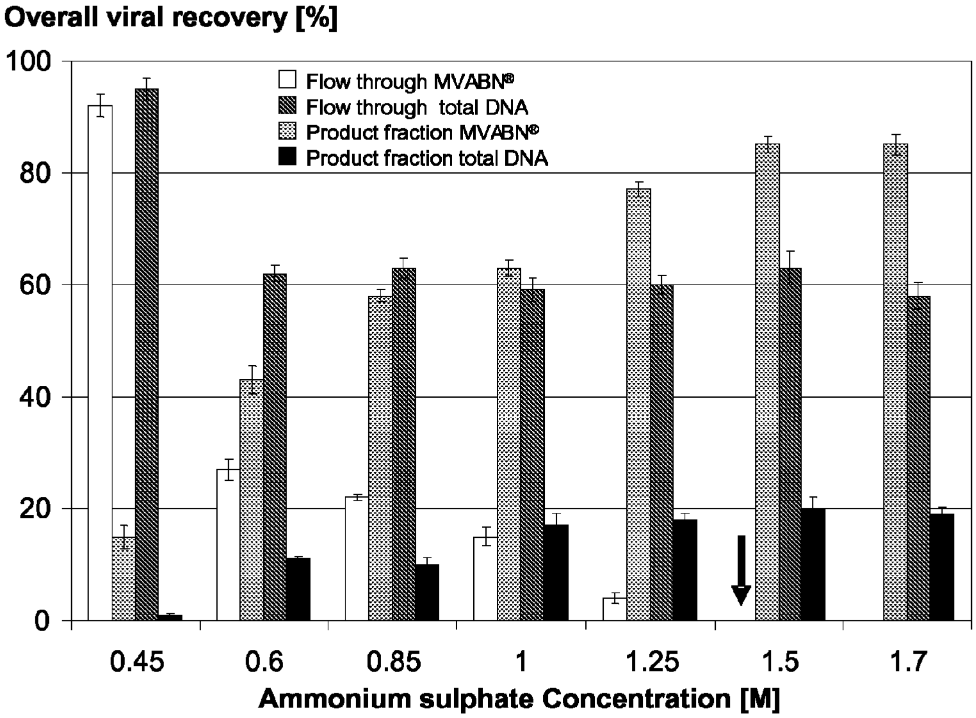
FIG. 3 depicts determination of the optimal salt concentration for MVA-BN® adsorption to 1 ml ToyoScreen® Phenyl matrix. Relative amounts of MVA-BN® virus particles (ELISA) in the flow through and product fraction as well as total dsDNA (DNA; Quant-iT® PicoGreen®) in the flow through and product fraction. Adsorption buffer: 1.7, 1.5, 1.25, 1, 0.85, 0.6 and 0.45 M $(NH_4)_2SO_4$, 50 mM $K_2HPO_4$, pH 7.4; elution buffer: 50 mM $K_2HPO_4$, pH 7.4. The chromatographic experiments were conducted twice and individual samples were analyzed in duplicates (dsDNA-assay) and triplicates (ELISA) as described in the material and method section; error bars: mean and standard deviation of each test series.

The main function of the HIC was the further reduction of the DNA contamination. This could be done in a positive or negative adsorption mode or alternatively, via a differential elution of virus particles and DNA. The potential applicability of HIC-resins for this task was clearly demonstrated by the combination of the pseudo-affinity MA and the HIC-phenyl resins (FIG. 3). Following studies focused for the most promising HIC-ligand (phenyl) on the reduction of the required ammonium sulfate concentration to promote the adsorption of virus particles or DNA. At the concentration of 0.45 M ammonium sulfate 95% of the DNA and 92% MVA-BN® virus particles did not adsorb to the HIC-phenyl resin. Increasing ammonium sulfate concentrations led to a sudden increase of DNA adsorption of approximately 40% which was constant over the range of tested ammonium sulfate concentrations (0.6 M to 1.7 M).

The amount of DNA in the product fraction ranged from 10% to 20%. Ammonium sulfate concentrations larger than 0.45 M resulted in steady increasing virus adsorption. At 0.6 M, 0.85 M, 1.0 M, 1.25 M, 1.5 M and 1.7 M ammonium sulfate about 43%, 58%, 63%, 77%, 85% and 85%, respectively, MVA-BN® virus particles were adsorbed and found subsequently in the product fraction. After 1.5 M ammonium sulfate no virus particles were detected in the flow through fraction. The DNA content in the eluted product fractions did not vary significantly at salt concentrations applicable for virus adsorption and can therefore be neglected for the selection of the optimal ammonium sulfate concentration of the adsorption buffer. The obtained results also clearly indicate that a differential elution of virus particles and DNA can not be achieved by a partial reduction of the ammonium sulfate concentration during the elution step. However, only roughly 40% of the DNA did adsorb to the HIC-phenyl resin at relevant ammonium sulfate concentrations, from which approximately 20% could not be eluted under the applied conditions for virus elution. Hence, the HIC phenyl resin represents a potential tool for a further DNA reduction by nearly 80%. The optimal salt concentration was judged based on the lowest possible ammonium sulfate concentration allowing complete virus adsorption (1.5 M ammonium sulfate). However, for reasons of process stability 1.7 M ammonium sulfate were used for the following studies. Comparing the resulting ammonium sulfate concentration with literature shows that for many different biomolecules ammonium sulfate concentrations of 1.5 to 2.0 M are sufficient for high yield recoveries without denaturation (Kato et al. 2004). However, especially the denaturation aspect depends mainly on the target and contaminating molecules.

Virus Infectivity after Downstream Processing

The effect of the described downstream process and especially the high ammonium sulfate concentration on the virus infectivity was tested via the $TCID_{50}$ assay. Therefore, representative samples were selected after a SC-MA or heparin-MA and HIC-phenyl combination, with adsorption buffers containing 1.7 M ammonium sulfate. Each product fraction of the triplicate chromatographic runs were assayed and the average $TCID_{50}$ determined. The initial $TCID_{50}$ (blank for this particular assays) of the homogenized and clarified harvest was $4.2\times10^7$ for this particular experiment. The average $TCID_{50}$ from the final product fractions of the SC-MA/HIC-phenyl, and heparin-MA/HIC-phenyl downstream processes were $1.7\times10^7$ and $1.6\times10^7$ $TCID_{50}$, respectively. Hence, the entire process including HIC-adsorption, led to an approximate reduction of the $TCID_{50}$ of 0.3 log units. The overall relative losses of the virus particles based on the ELISA quantification of the initially loaded sample were on average for both processes 47% (FIG. 2), which corresponds to approximately 0.3 log units from the $TCID_{50}$. Therefore, it can be concluded that losses on virus infectivity were not significantly impacted by the high concentration of ammonium sulfate.

REFERENCES

Abdalrhman I, Gurt I, Katz E. 2006. Protection induced in mice against a lethal *orthopox* virus by the Lister strain of vaccinia virus and modified vaccinia virus Ankara (MVA). Vaccine 24(19):4152-4160.

Amosenko F A, Svitkin Y V, Popova V D, Terletskaya E N, Timofeev A V, Elbert L B, Lashkevich V A, Drozdov S G. 1991. Use of protamine sulphate for elimination of substrate DNA in poliovaccines produced on continuous cell lines. Vaccine 9(3):207-209.

Dancis B M. 1978. Shear breakage of DNA. 24(2):489-503.

Deshmukh N R, Lali A M. 2005. Adsorptive purification of pDNA on superporous rigid cross-linked cellulose matrix. Journal of Chromatography B 818(1):5-10.

Diogo M M, Queiroz J A, Prazeres D M F. 2001. Studies on the retention of plasmid DNA and *Escherichia coli* nucleic acids by hydrophobic interaction chromatography. Bioseparation 10(4):211-220.

Diogo M M, Queiroz J A, Prazeres D M F. 2005. Chromatography of plasmid DNA. Journal of Chromatography A 1069(1):3-22.

Diogo M M, Ribeiro S, Queiroz J A, Monteiro G A, Perrin P, Tordo N, Prazeres D M F. 2000. Scale-up of hydrophobic interaction chromatography for the purification of a DNA vaccine against rabies. Biotechnology Letters 22(17): 1397-1400.

Esteban M, Metz D H. 1973. Early virus protein synthesis in vaccinia virus-infected cells. J Gen Virol 19(2):201-6.

Freitas S S, Santos J A L, Prazeres D M F. 2009. Plasmid purification by hydrophobic interaction chromatography using sodium citrate in the mobile phase. Separation and Purification Technology 65(1):95-104.

Gagnon P, Ng P, Zhen J, Aberin C, He J, Mekosh H, Cummings L, Zaidi S, Richieri R. 2006. Simultaneous Removal of Leached Protein A, Aggregates, DNA, and Endotoxins from MAbs. BioProcess International Vol. 4, No. 2: pp 50-60 4(2):50-60.

Gijsbers L, Koel Br, Weggeman M, Goudsmit J, Havenga M, Marzio G. 2005. Quantification of Residual Host Cell DNA in Adenoviral Vectors Produced on PER.C6Â® Cells. Hum. Gene Ther. 16(3):393-398.

Goerke A R, To B C S, Lee A L, Sagar S L, Konz J O. 2005. Development of a novel adenovirus purification process utilizing selective precipitation of cellular DNA. Biotechnology and Bioengineering 91(1):12-21.

Graumann K, Ebenbichler A A. 2005. Development and Scale up of Preparative HIC for the Purification of a Recombinant Therapeutic Protein. Chemical Engineering & Technology 28(11):1398-1407.

Greenberg R N, Kennedy J S. 2008. ACAM2000: a newly licensed cell culture-based live vaccinia smallpox vaccine. Expert Opinion on Investigational Drugs 17(4):555-564.

Halder E, Chattoraj D K, Das K P. 2005. Adsorption of biopolymers at hydrophilic cellulose-water interface. Biopolymers 77(5):286-295.

Iuliano S, Fisher J R, Chen M, Kelly W J. 2002. Rapid analysis of a plasmid by hydrophobic-interaction chromatography with a non-porous resin. Journal of Chromatography A 972(1):77-86.

Joklik W K. 1962. The preparation and characteristics of highly purified radioactively labelled poxvirus. Biochimica et Biophysica Acta (BBA)—Specialized Section on Nucleic Acids and Related Subjects 61(2):290-301.

Jordan I, Vos A, Beilfuβ S, Neubert A, Breul S, Sandig V. 2009. An avian cell line designed for production of highly attenuated viruses. Vaccine 27(5):748-756.

Kalbfuss B, Wolff M, Morenweiser R, Reichl U. 2007. Purification of cell culture-derived human influenza A virus by size-exclusion and anion-exchange chromatography. Biotechnology and Bioengineering 96(5):932-944.

Kato Y, Nakamura K, Kitamura T, Hasegawa M, Sasaki H. 2004. Hydrophobic interaction chromatography at low salt concentration for the capture of monoclonal antibodies. Journal of Chromatography A 1036(1):45-50.

Knudsen H L, Fahrner R L, Xu Y, Norling L A, Blank G S. 2001. Membrane ion-exchange chromatography for process-scale antibody purification. Journal of Chromatography A 907(1-2):145-154.

Konz J O, Lee A L, Lewis J A, Sagar S L. 2005. Development of a Purification Process for Adenovirus: Controlling Virus Aggregation to Improve the Clearance of Host Cell DNA. Biotechnology Progress 21(2):466-472.

Kramarczyk J F, Kelley B D, Coffman J L. 2008. High-throughput screening of chromatographic separations: II. Hydrophobic interaction. Biotechnology and Bioengineering 100(4):707-720.

Kumar A A P, Rao Y U B, Leo William Joseph A, Mani K R, Swaminathan K. 2002. Process standardization for optimal virus recovery and removal of substrate DNA and bovine serum proteins in Vero cell-derived rabies vaccine. Journal of Bioscience and Bioengineering 94(5):375-383.

Lu Y, Williamson B, Gillespie R. 2009. Recent Advancement in Application of Hydrophobic Interaction Chromatography for Aggregate Removal in Industrial Purification Process Curr Pharm Biotechnol 10(4):427-433.

Madalinski W, Bankovski A, Korbecki M. 1977. Purification of vaccinia virus by zonal centrifugation and analysis of viral protein composition. Acta virologica 21(2):104-108.

Mahn A, Asenjo J A. 2005. Prediction of protein retention in hydrophobic interaction chromatography. Biotechnology Advances 23(5):359-368.

Monath T P, Caldwell J R, Mundt W, Fusco J, Johnson C S, Buller M, Liu J, Gardner B, Downing G, Blum P S and others. 2004. ACAM2000 clonal Vero cell culture vaccinia virus (New York City Board of Health strain)—a second-generation smallpox vaccine for biological defense. International Journal of Infectious Diseases 8(Supplement 2):31-44.

Opitz L, Lehmann S, Reichl U, Wolff M W. 2009. Sulfated membrane adsorbers for economic pseudo-affinity capture of influenza virus particles. Biotechnol. and Bioeng. 103 (6):1144-1154.

Opitz L, Salaklang J, Buttner H, Reichl U, Wolff M W. 2007. Lectin-affinity chromatography for downstream processing of MDCK cell culture derived human influenza A viruses. Vaccine 25(5):939-947.

Opitz L, Zimmermann A, Lehmann S, Genzel Y, Lübben H, Reichl U, Wolff M W. 2008. Capture of cell culture-derived influenza virus by lectins: Strain independent, but host cell dependent. Journal of Virological Methods 154(1-2):61-68.

Påhlman S, Rosengren J, Hjertén S. 1977. Hydrophobic interaction chromatography on uncharged Sepharose® derivatives: Effects of neutral salts on the adsorption of proteins. Journal of Chromatography A 131:99-108.

Payne L G, Norrby E. 1976. Presence of Haemagglutinin in the Envelope of Extracellular Vaccinia Virus Particles. J Gen Virol 32(1):63-72.

Queiroz J A, Tomaz C T, Cabral J M S. 2001. Hydrophobic interaction chromatography of proteins. Journal of Biotechnology 87(2):143-159.

Sakata M, Kunitake M. 2007. Chromatographic Removal of DNA from Protein Solutions by Cationic Polymer Beads. Current Pharmaceutical Analysis 3:170-179.

Sakata M, Nakayama M, Fujisaki T, Morimura S, Kunitake M, Hirayama C. 2005. Chromatographic Removal of Host Cell DNA from Cellular Products Using Columns Packed with Cationic Copolymer Beads. Chromatographia 62(9): 465-470.

Sheng-Fowler L, Lewis Jr A M, Peden K. 2009. Issues associated with residual cell-substrate DNA in viral vaccines. Biologicals 37(3):190-195.

Stickl H, Korb W, Hochstein-Mintzel V. 1970. Purifying the vaccinia virus vaccine by gel filtration. Zentralblatt fur Bakteriologie, Parasitenkunde, Infektionskrankheiten und Hygiene. 1. Abt. Medizinisch-hygienische Bakteriologie, Virusforschung und Parasitologie. 215(1):38-50.

Tauer C, Buchacher A, Jungbauer A. 1995. DNA clearance in chromatography of proteins, exemplified by affinity chromatography. Journal of Biochemical and Biophysical Methods 30(1):75-78.

Transfiguracion J, Jaalouk D E, Ghani K, Galipeau J, Kamen A. 2003. Size-Exclusion Chromatography Purification of High-Titer Vesicular Stomatitis Virus G Glycoprotein-Pseudotyped Retrovectors for Cell and Gene Therapy Applications. Hum. Gene Ther. 14(12):1139-1153.

Triyoso D H, Good T A. 1999. Pulsatile shear stress leads to DNA fragmentation in human SH-SY5Y neuroblastoma cell line. The Journal of Physiology 515(2):355-365.

Tsumoto K, Ejima D, Nagase K, Arakawa T. 2007. Arginine improves protein elution in hydrophobic interaction chromatography: The cases of human interleukin-6 and activin-A. Journal of Chromatography A 1154(1-2):81-86.

Ueberbacher R, Haimer E, Hahn R, Jungbauer A. 2008. Hydrophobic interaction chromatography of proteins: V. Quantitative assessment of conformational changes. Journal of Chromatography A 1198-1199:154-163.

Wolff M W, Reichl U. 2008. Downstream Processing: From Egg to Cell Culture-Derived Influenza Virus Particles. Chemical Engineering & Technology 31(6):846-857.

Wolff M W, Siewert C, Lehmann S, Post Hansen S, Djurup R, Faber R, Reichl U. 2009. Capturing of cell culture-derived modified Vaccinia Ankara virus by ion exchange and pseudo-affinity membrane adsorbers, Biotechnology and Bioengineering Processing, DOI 10.1002/bit.22595.

World-Health-Organization. 1998. WHO Expert Committee on Biological Standardization. Worl Health Organ. Tech. Rep. Ser. 878(i-vi):1-101.

Zwartouw H T, Westwood J, Appleyard G. 1962. Purification of pox viruses by density-gradient centrifugation. Journal of General Microbiology 29:523-529.

We claim:

1. A purified vaccinia virus preparation comprising less than 100 ng of cellular DNA per $10^8$ $TCID_{50}$ of the vaccinia virus, wherein the vaccinia virus preparation has not been treated with a nuclease.

2. The purified vaccinia virus preparation of claim 1, wherein the vaccinia virus preparation comprises $10^8$ $TCID_{50}$ of the vaccinia virus.

3. The purified vaccinia virus preparation of claim 1, wherein the vaccinia virus preparation comprises more than $5\times10^{11}$ $TCID_{50}$ of the vaccinia virus.

4. The purified vaccinia virus preparation of claim 1, wherein the vaccinia virus preparation comprises less than 50 ng of cellular DNA per $10^8$ $TCID_{50}$ of the vaccinia virus.

5. The purified vaccinia virus preparation of claim 1, wherein the vaccinia virus preparation comprises less than 20 ng of cellular DNA per $10^8$ $TCID_{50}$ of the vaccinia virus.

6. The purified vaccinia virus preparation of claim 1, wherein the vaccinia virus is a modified vaccinia Ankara virus.

7. The purified vaccinia virus preparation of claim 2, wherein the vaccinia virus is a modified vaccinia Ankara virus.

8. The purified vaccinia virus preparation of claim 3, wherein the vaccinia virus is a modified vaccinia Ankara virus.

9. The purified vaccinia virus preparation of claim 4, wherein the vaccinia virus is a modified vaccinia Ankara virus.

10. The purified vaccinia virus preparation of claim 5, wherein the vaccinia virus is a modified vaccinia Ankara virus.

11. A purified vaccinia virus preparation comprising less than 10 ng of cellular DNA per $10^8$ $TCID_{50}$ of the vaccinia virus, wherein the vaccinia virus preparation has not been treated with a nuclease.

12. The purified vaccinia virus preparation of claim 11, wherein the vaccinia virus preparation comprises $10^8$ $TCID_{50}$ of the vaccinia virus.

13. The purified vaccinia virus preparation of claim 11, wherein the vaccinia virus preparation comprises more than $5\times10^{11}$ $TCID_{50}$ of the vaccinia virus.

14. The purified vaccinia virus preparation of claim 11, wherein the vaccinia virus is a modified vaccinia Ankara virus.

15. The purified vaccinia virus preparation of claim 12, wherein the vaccinia virus is a modified vaccinia Ankara virus.

16. The purified vaccinia virus preparation of claim 13, wherein the vaccinia virus is a modified vaccinia Ankara virus.

* * * * *